(12) United States Patent
Esashi et al.

(10) Patent No.: US 10,448,912 B2
(45) Date of Patent: Oct. 22, 2019

(54) IMAGE PROCESSING APPARATUS

(71) Applicant: Toshiba Medical Systems Corporation, Otawara-shi (JP)

(72) Inventors: Satoru Esashi, Nasushiobara (JP); Jun Okada, Nasushiobara (JP); Toshio Muroi, Nasushiobara (JP); Nobuo Ogura, Otawara (JP); Masanori Gunji, Otawara (JP); Nobuhiro Ohga, Nasushiobara (JP); Yoshimasa Kobayashi, Nasushiobara (JP); Naoko Kuratomi, Sakura (JP)

(73) Assignee: Canon Medical Systems Corporation, Otawara-shi (JP)

(*) Notice: Subject to any disclaimer, the term of this patent is extended or adjusted under 35 U.S.C. 154(b) by 193 days.

(21) Appl. No.: 15/480,842

(22) Filed: Apr. 6, 2017

(65) Prior Publication Data

US 2017/0295300 A1    Oct. 12, 2017

(30) Foreign Application Priority Data

Apr. 6, 2016 (JP) .................... 2016-076507
Apr. 4, 2017 (JP) .................... 2017-074527

(51) Int. Cl.
*H04N 1/60* (2006.01)
*A61B 6/00* (2006.01)
(Continued)

(52) U.S. Cl.
CPC .............. *A61B 6/469* (2013.01); *A61B 6/461* (2013.01); *A61B 6/5217* (2013.01);
(Continued)

(58) Field of Classification Search
CPC ....... A61B 6/469; A61B 6/5217; A61B 6/461; H04N 1/407; H04N 1/405; G06T 11/001
See application file for complete search history.

(56) References Cited

U.S. PATENT DOCUMENTS 6,714,208 B1    3/2004    Yamaguchi
6,714,320 B1    3/2004    Nakahara et al.
(Continued)

FOREIGN PATENT DOCUMENTS

| JP | 2000-330530 | 11/2000 |
|---|---|---|
| JP | 2001-61063 | 3/2001 |
| JP | 2011-23895 | 2/2011 |

*Primary Examiner* — Yon J Couso
(74) *Attorney, Agent, or Firm* — Oblon, McClelland, Maier & Neustadt, L.L.P.

(57) ABSTRACT

An image processing apparatus comprises processing circuitry. The processing circuitry is configured to acquire a first image in which each pixel is expressed with a first gradation. And the processing circuitry is configured to specify a partial region in the first image. And the processing circuitry is configured to convert, based on correspondence information that associates each level of the first gradation with a display pattern of a plurality of pixels in a display, the level in the first gradation of each pixel included in the partial region in the first image into the corresponding display pattern, the display displaying the display pattern with a second gradation having fewer levels than the first gradation. And the processing circuitry is configured to generate a second image that expresses a plurality of pixels included in the partial region of the first image as the converted display patterns.

18 Claims, 12 Drawing Sheets

(51) Int. Cl.
*G06T 11/00* (2006.01)
*H04N 1/405* (2006.01)
*H04N 1/407* (2006.01)

(52) U.S. Cl.
CPC ........... *G06T 11/001* (2013.01); *H04N 1/405* (2013.01); *H04N 1/407* (2013.01)

(56) References Cited

U.S. PATENT DOCUMENTS

| | | |
|---|---|---|
| 6,906,825 B1 | 6/2005 | Nakahara et al. |
| 2005/0190610 A1* | 9/2005 | Furukawa ............ G09G 3/2055 365/189.05 |
| 2007/0176949 A1* | 8/2007 | Chang ................. G09G 3/2048 345/690 |
| 2010/0026722 A1* | 2/2010 | Kondo ................ G09G 3/2007 345/660 |

* cited by examiner

ORIGINAL DATA

WITHOUT DITHERING

WITH DITHERING

IMAGE PROCESSING APPARATUS

CROSS-REFERENCE TO RELATED APPLICATIONS

This application is based upon and claims the benefit of priority from Japanese Patent Application No. 2016-76507, filed on Apr. 6, 2016; and Japanese Patent Application No. 2017-74527, filed on Apr. 4, 2017, the entire contents of all of which are incorporated herein by reference.

FIELD

Embodiments described herein relate generally to an image processing apparatus.

BACKGROUND

An X-ray diagnostic apparatus irradiates a subject with X-rays, and based on the transmitted X-rays, generates an X-ray image representing differences in attenuation of the X-rays in a subject with black-and-white density. Such an X-ray image is displayed on various types of displays, and is viewed when, for example, a contrast radiography examination, such as an angiography, or an interventional treatment is performed. The black-and-white gradation in the X-ray image generated by the X-ray diagnostic apparatus is converted into a gradation expressed by a display when displayed on the display.

DETAILED DESCRIPTION

According to an embodiment, an image processing apparatus comprises processing circuitry. The processing circuitry is configured to acquire a first image in which each pixel is expressed with a first gradation. And the processing circuitry is configured to specify a partial region in the first image. And the processing circuitry is configured to convert, based on correspondence information that associates each level of the first gradation with a display pattern of a plurality of pixels in a display, the level in the first gradation of each pixel included in the partial region in the first image into the corresponding display pattern, the display displaying the display pattern with a second gradation having fewer levels than the first gradation. And the processing circuitry is configured to generate a second image that expresses a plurality of pixels included in the partial region of the first image as the converted display patterns.

The following describes an image processing apparatus according to embodiments, with reference to the drawings. The following describes, as an example, an X-ray diagnostic apparatus including an image processing apparatus according to the embodiments. The following describes X-ray images as examples of images subjected to image processing by the image processing apparatus according to the embodiments.

Figure 1:
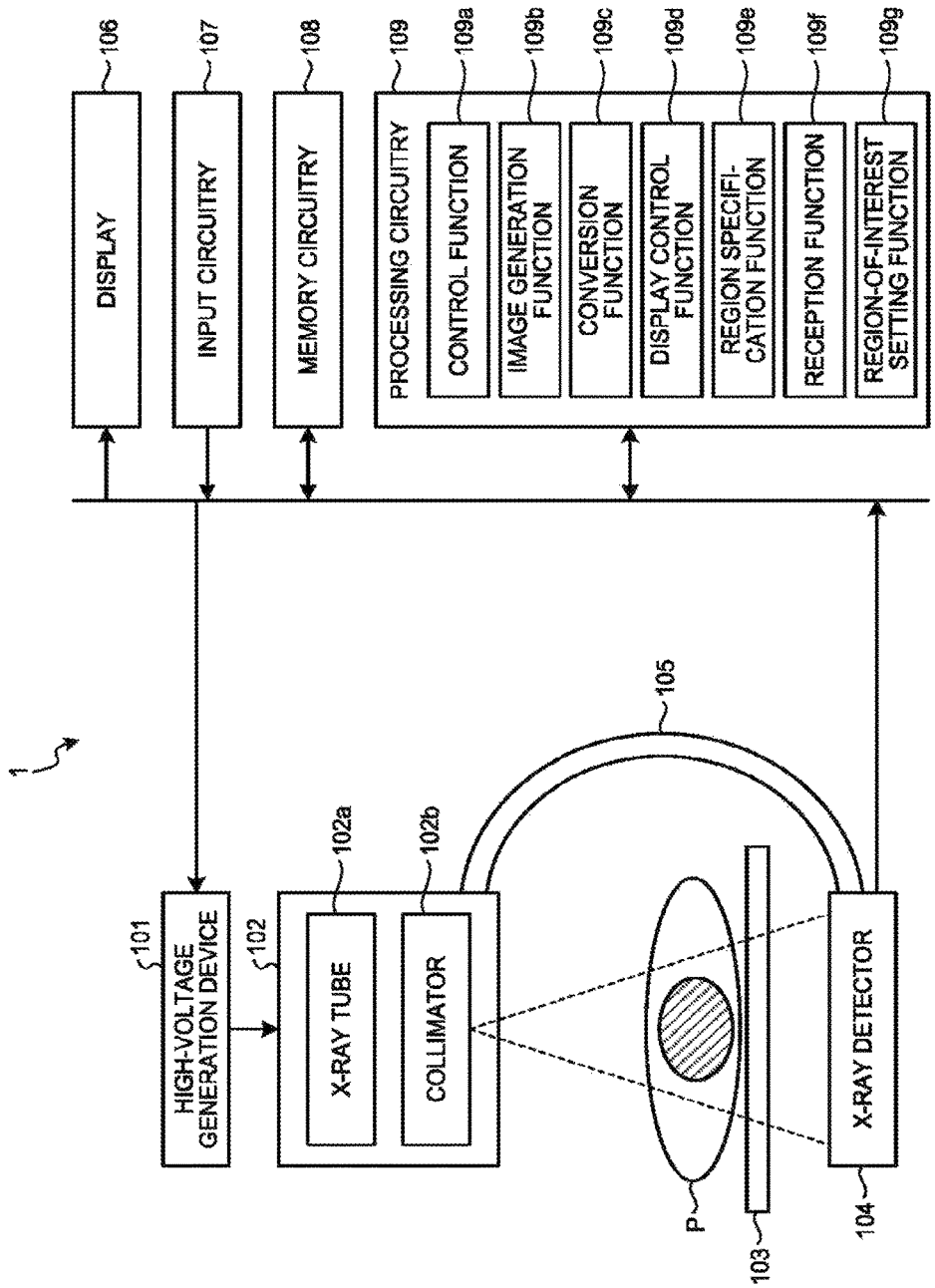
FIG. 1 is a block diagram illustrating a configuration example of an X-ray diagnostic apparatus according to a first embodiment.

First, a configuration example of an X-ray diagnostic apparatus 1 according to a first embodiment will be described using FIG. 1. FIG. 1 is a block diagram illustrating the configuration example of the X-ray diagnostic apparatus 1 according to the first embodiment. As illustrated in FIG. 1, the X-ray diagnostic apparatus 1 according to the first embodiment includes a high-voltage generation device 101, an X-ray source 102, a tabletop 103, an X-ray detector 104, an arm 105, a display 106, input circuitry 107, memory circuitry 108, and processing circuitry 109.

Under control by the processing circuitry 109, the high-voltage generation device 101 generates a high voltage, and supplies the generated high voltage to the X-ray source 102. The X-ray source 102 includes an X-ray tube 102a and a collimator 102b. The X-ray tube 102a uses the high voltage supplied from the high-voltage generation device 101 to generate X-rays. The collimator 102b controls the radiation field of the X-rays in order to reduce the radiation exposure amount of a subject P and improve the image quality of the image.

The tabletop 103 is a bed on which the subject P lies down, and is disposed on top of a couch (not illustrated). The X-ray detector 104 including a plurality of X-ray detection elements detects distribution data of signal intensity of the X-rays transmitted through the subject P, and transmits the detected distribution data to the processing circuitry 109. The X-ray source 102 and the X-ray detector 104 are held by the arm 105 so as to face each other across the subject P.

The display 106 is a monitor referred to by an operator, and displays various types of the X-ray images under the control by the processing circuitry 109. The display 106 may be a stationary monitor, or a display screen of a portable terminal (for example, a portable personal computer (PC), such as a laptop PC or a tablet PC, a personal digital assistant (PDA), or a mobile phone). The display 106 displays, for example, an X-ray image having been subjected to pseudo gradation processing, and the X-ray image not having been subjected to the pseudo gradation processing. The X-ray image displayed by the display 106 and the pseudo gradation processing will be described later. The following describes, as an example, a case where the display 106 is a color monitor that displays the image with a gradation of "8-bits (256 gradation levels)" for each of red, green, and blue (RGB) colors.

The input circuitry 107 includes, for example, a mouse, a keyboard, a trackball, switches, buttons, and a joystick used for input of various instructions and various settings, and transfers information on the instructions and the settings received from the operator to the processing circuitry 109. The input circuitry 107 receives from the operator, for example, an operation to specify a partial region of the X-ray image displayed on the display 106. The input circuitry 107 also receives from the operator, for example, a switching operation of a display mode. The method of specifying the partial region and the display mode will be described later.

The memory circuitry 108 stores data used when the processing circuitry 109 controls the overall processing performed by the X-ray diagnostic apparatus 1. For example, the memory circuitry 108 stores programs to be executed by the processing circuitry 109. The memory circuitry 108 also stores various types of image data. The memory circuitry 108 also stores correspondence information that associates each level of the gradation of the X-ray image with a display pattern of a plurality of pixels in the display 106. The correspondence information will be described later.

The processing circuitry 109 performs a control function 109a, an image generation function 109b, a conversion function 109c, a display control function 109d, a region specification function 109e, a reception function 109f, and a region-of-interest setting function 109g (hereinafter, abbreviated as ROI setting function 109g). In the embodiment illustrated in FIG. 1, the processing functions implemented by the control function 109a, the image generation function 109b, the conversion function 109c, the display control function 109d, the region specification function 109e, the reception function 109f, and the ROI setting function 109g are recorded in the form of the computer-executable programs in the memory circuitry 108. The processing circuitry 109 is a processor that reads out and executes the programs from the memory circuitry 108 to perform the functions corresponding to the respective programs. In other words, in the state of having read out the programs, the processing circuitry 109 has the functions illustrated in the processing circuitry 109 of FIG. 1. The description has been made with reference to FIG. 1 that the single processing circuitry performs the processing functions implemented by the control function 109a, the image generation function 109b, the conversion function 109c, the display control function 109d, the region specification function 109e, the reception function 109f, and the ROI setting function 109g. The processing circuitry may, however, be configured by combining a plurality of independent processors, and the processors may execute the programs to perform the functions.

The term "processor" refers to, for example, a central processing unit (CPU), a graphics processing unit (GPU), or a circuit, such as an application-specific integrated circuit (ASIC), or a programmable logic device (such as a simple programmable logic device (SPLD), a complex programmable logic device (CPLD), or a field-programmable gate array (FPGA)). The processor reads out and executes the programs stored in the memory circuitry 108 to perform the functions. Instead of being stored in the memory circuitry 108, the programs may be directly incorporated into the circuit of the processor. In this case, the processor reads out and executes the programs stored in the circuit. Each of the processors of the present embodiment is not limited to being configured as a single circuit on a processor-by-processor basis. A plurality of independent circuits may be combined to be configured as one processor, and the functions thereof may be performed. Moreover, the components illustrated in FIG. 1 may be integrated into one processor, and the functions thereof may be performed.

The image generation function 109b in the first embodiment is an example of image generation processing performed by processing circuitry described in the claims. The conversion function 109c in the first embodiment is an example of conversion processing performed by the processing circuitry described in the claims. The display control function 109d in the first embodiment is an example of display control processing performed by the processing circuitry described in the claims. The region specification function 109e in the first embodiment is an example of region specification processing performed by the processing circuitry described in the claims. The reception function 109f in the first embodiment is an example of reception processing performed by the processing circuitry described in the claims. The ROI setting function 109g in the first embodiment is an example of region-of-interest setting processing performed by the processing circuitry described in the claims.

The processing circuitry 109 controls the overall processing performed by the X-ray diagnostic apparatus 1. The processing performed by the X-ray diagnostic apparatus 1 refers to, for example, a series of processing, such as acquiring the X-ray image and display of the X-ray image, related to examinations using the X-ray image. For example, the processing circuitry 109 controls acquisition processing of projection data. Also, for example, the processing circuitry 109 generates the X-ray images using the acquired projection data. The processing circuitry 109 stores the generated various X-ray images in the memory circuitry 108.

The processing circuitry 109 specifies the partial region in the X-ray image stored in the memory circuitry 108. The processing circuitry 109 converts, based on the correspondence information stored in the memory circuitry 108, the level of gradation of each of the pixels included in the partial region in the generated the X-ray image into the corresponding display pattern. The processing circuitry 109 generates an X-ray image that represents the pixels included in the partial region of the X-ray image generated based on the projection data as the display patterns converted based on the correspondence information. The processing circuitry 109 displays the X-ray image represented as the display patterns on the display 106. This processing will be described later.

The above has described the overall configuration of the X-ray diagnostic apparatus 1 according to the first embodiment. Under this configuration, the X-ray diagnostic apparatus 1 according to the first embodiment converts the gradation of each of the pixels in the X-ray image generated based on the X-rays transmitted through the subject P into the corresponding display pattern based on the predetermined correspondence information so as to generate the X-ray image representing the pixels as the display patterns, and thus improves accuracy of the examinations using the X-ray image.

First, a description will be made of the conversion of the gradation in the case of displaying the X-ray image on the display 106. For example, in the case where the X-ray diagnostic apparatus 1 generates the X-ray image for display at "10-bits (1024 gradation levels)", and displays it on the display 106 of "8-bits (256 gradation levels)" (such as a display of 8-bits for each of RGB (256 colors)), the X-ray image in which black-and-white brightness is represented at "1024 levels" is converted into that with the brightness of "256 levels". In other words, the brightness of "four levels"

in the X-ray image is converted into the brightness of "one level", so that the pixels having different brightness levels in the X-ray are displayed at the same brightness level on the display 106.

If the number of colors is reduced at the display stage, the image viewed by a viewer lacks the original gradation information of the image, and may look like white non-gradation or contour lines. Hence, the X-ray diagnostic apparatus 1 according to the first embodiment applies the pseudo gradation processing to the X-ray image at a stage before the display of the X-ray image on the display 106, and displays the X-ray image representing the original gradation information in a pseudo manner on the display 106.

Figure 2:
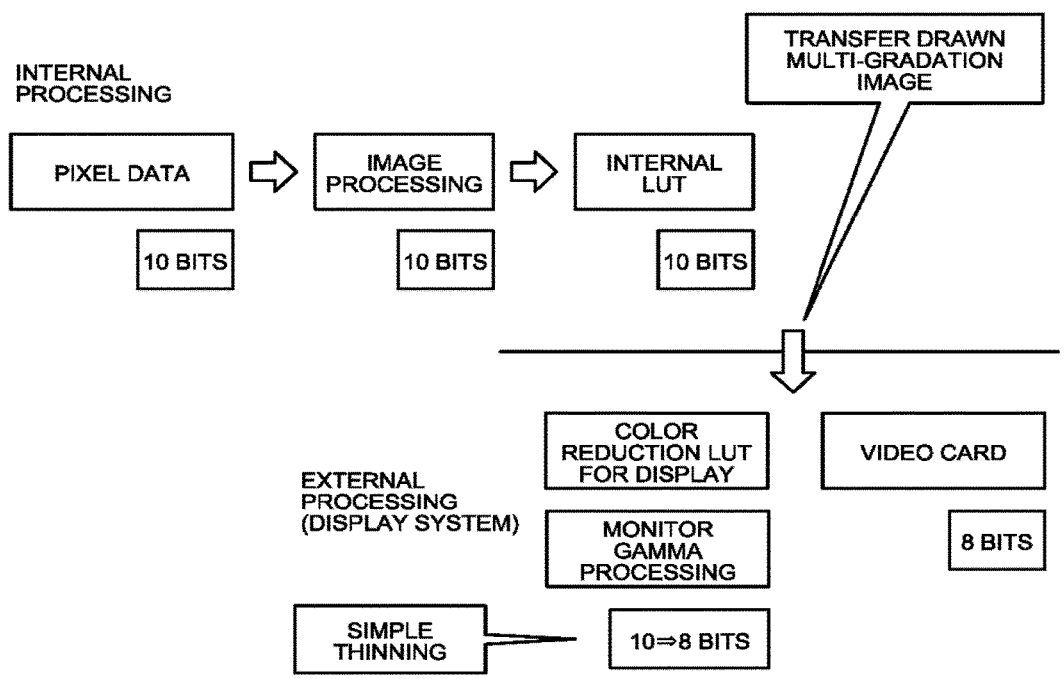
FIG. 2 is a diagram for explaining display of an X-ray image.

First, the following describes details of the conversion of the gradation performed by the X-ray diagnostic apparatus 1. FIG. 2 is a diagram for explaining the display of the X-ray image. The upper part of FIG. 2 illustrates processing (internal processing) on the main unit side of the X-ray diagnostic apparatus 1, and the lower part of FIG. 2 illustrates processing (external processing) on the display system side (such as the display 106 side) of the X-ray diagnostic apparatus 1. For example, as illustrated in the upper part of FIG. 2, the X-ray diagnostic apparatus 1 applies image processing to the pixel data (projection data) detected by the X-ray detector 104, and applies an internal lookup table (LUT) to generate a multi-gradation X-ray image. In other words, for example, as illustrated in the upper part of FIG. 2, the main unit side of the X-ray diagnostic apparatus 1 processes the "10-bits" data in the processing from the pixel data to the X-ray image. In the X-ray diagnostic apparatus 1, the data stored in the memory circuitry 108 remains to be "10-bits" data.

In the case of displaying the generated X-ray image on the display 106, the display system receives the multi-gradation X-ray image, applies a color reduction LUT for display, and performs monitor gamma processing to convert the gradation of the X-ray image from "10-bits" to "8-bits". A video card putouts the "8-bits" X-ray image from the display 106. In this manner, in the case of displaying the X-ray image having a larger number of gradation levels than the number of gradation levels displayed by the display 106, the X-ray diagnostic apparatus 1 simply thins the number of gradation levels according to the LUT kept in the display 106, and displays the X-ray image.

Figure 3:
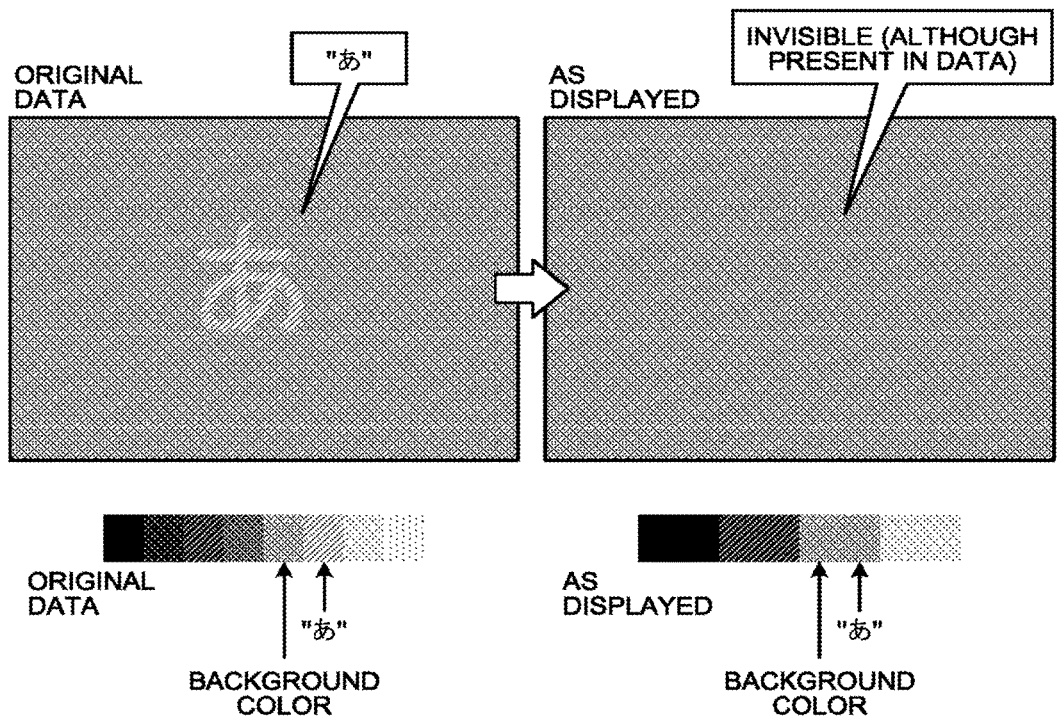
FIG. 3 is a diagram for explaining the display of the X-ray image.

The X-ray diagnostic apparatus 1 according to the first embodiment applies the pseudo gradation processing to the X-ray image before performing the conversion processing of the gradation, and displays the X-ray image having the original gradation information even after the color reduction LUT for display is applied. As a result, for example, information that has become invisible due to the conversion processing of the gradation by the simply thinning can be displayed. FIG. 3 is a diagram for explaining the display of the X-ray image. The left side of FIG. 3 illustrates the original data of the X-ray image before being displayed on the display 106 (at the stage of the internal processing), and the right side of FIG. 3 illustrates the X-ray image displayed via the simple thinning.

For example, as illustrated in FIG. 3, assume that the generated X-ray image includes a character " 💩 " as information. In this case, since the original data is multi-gradation data, the portion of the character " 💩 " and the background portion differ in level of gradation, and thus differ in color from each other. However, if the gradation of the original data is simply converted, the colors of the portion of the character " 💩 " and the background portion are converted into the same color, as illustrated by a diagram on the right side of FIG. 3, and are indistinguishable from each other as information. Hence, the X-ray diagnostic apparatus 1 performs the pseudo gradation processing before performing the conversion to the gradation displayable by the display 106, and displays the X-ray image in which the information is distinguishable even after the conversion to the gradation of the display 106 is performed. In other words, the X-ray diagnostic apparatus 1 displays, on the display 106, the X-ray image in which the character " 💩 " is distinguishable when the X-ray image of FIG. 3 is displayed on the display 106. The following describes in detail the processing performed by the X-ray diagnostic apparatus 1 according to the first embodiment.

First, the control function 109*a* acquires the projection data by controlling an imaging system including the high-voltage generation device 101, the X-ray source 102, the tabletop 103, the X-ray detector 104, and the arm 105. Specifically, the control function 109*a* controls the imaging system described above to expose the subject P to the X-rays, and to detect the X-rays transmitted through the subject P using the X-ray detector 104. The control function 109*a* uses electric signals converted from the X-rays by the X-ray detector 104 to generate the projection data, and stores the generated projection data in the memory circuitry 108. The control function 109*a* performs, for example, a current-voltage conversion, an analog-digital (A/D) conversion, and a parallel-serial conversion on the electric signals received from the X-ray detector 104 to generate the projection data (pixel data).

Then, the image generation function 109*b* generates the X-ray image using the acquired projection data (pixel data). Specifically, the image generation function 109*b* applies various types of image processing to the projection data (pixel data), and applies the internal LUT to generate the X-ray image. Hereinafter, the X-ray image generated by the image generation function 109*b* based on the X-rays transmitted through the subject P will also be referred to as a first X-ray image. The first X-ray image is an example of a first image described in the claims.

The conversion function 109*c* converts the level in a first gradation of each of the pixels in the first X-ray image into the corresponding display pattern based on the correspondence information that associates each level of the first gradation with the display pattern of a plurality of pixels in the display 106 displayed with a second gradation having fewer levels than the first gradation. The display control function 109*d* displays, on the display 106, the X-ray image represented as the display patterns acquired by converting the pixels included in the partial region of the first X-ray image by the conversion function 109*c*. The following describes the above-described processes, using FIG. 4. The following describes, as an example, a case where the first X-ray image is a black-and-white image in which the first X-ray image has a gradation of "10-bits (1024 gradation levels)". The gradation of the black-and-white image refers to a gradation in brightness of hues expressed in the X-ray image. Hereinafter, the gradation represented by each of the pixels of the first X-ray image is also referred to as the first gradation. Hereinafter, the gradation represented by each of the pixels of the display 106 is also referred to as the second gradation. The following describes, as an example, a case where the first gradation has more levels than the second gradation.

Figure 4:
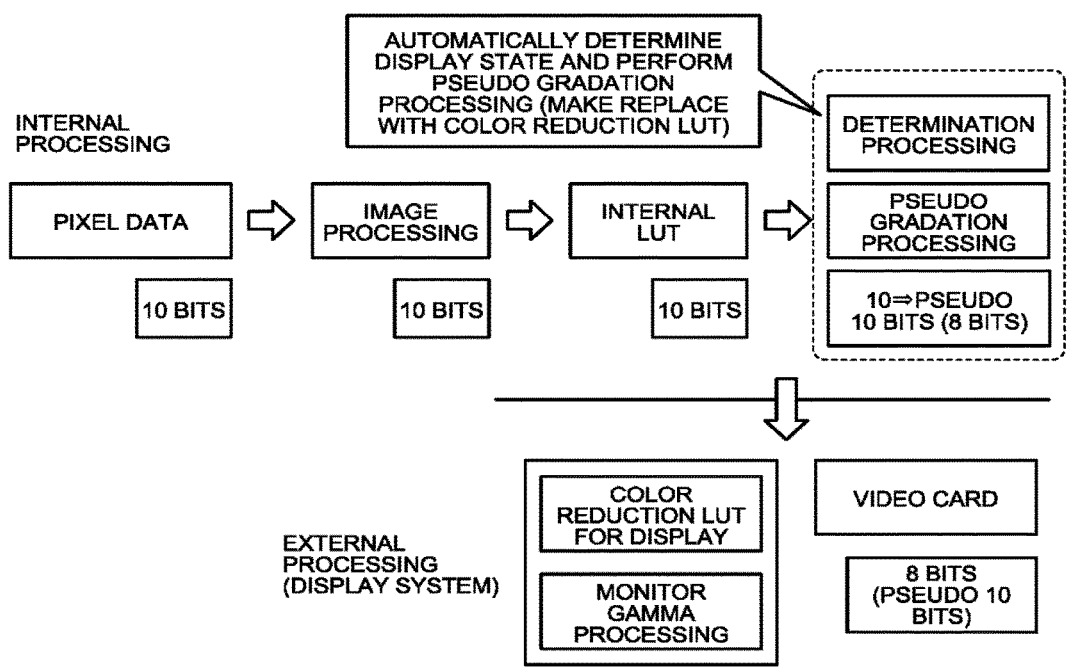
FIG. 4 is a diagram for explaining the display of the X-ray image according to the first embodiment.
Figure 5:
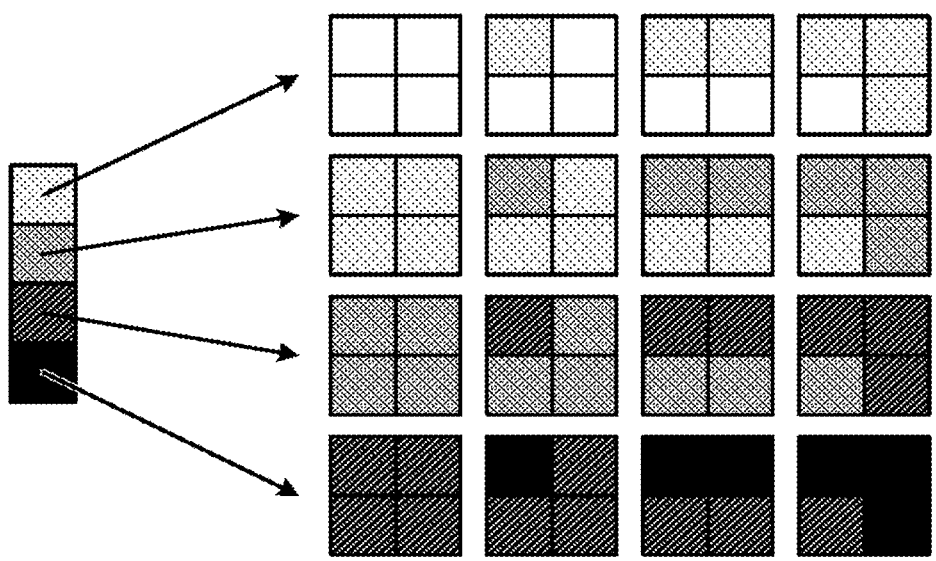
FIG. 5 is a diagram for explaining pseudo gradation processing according to the first embodiment.

As illustrated in FIG. 4, prior to the output of the first X-ray image to the display 106 after the image generation function 109*b* has generated the first X-ray image, the conversion function 109*c* determines whether to perform the pseudo gradation processing. And if the pseudo gradation processing is determined to be performed, the conversion function 109c applies the pseudo gradation processing to the first X-ray image. The pseudo gradation processing performed by the conversion function 109c refers to processing to represent the first gradation contained in the pixels of the first X-ray image using the second gradation displayed by the display 106 so as to represent the gradation information contained in the pixels of the first X-ray image on the display 106 in a pseudo manner. FIG. 4 is a diagram for explaining the display of the X-ray image according to the first embodiment. The upper part of FIG. 4 illustrates processing (internal processing) on the main unit side of the X-ray diagnostic apparatus 1, and the lower part of FIG. 4 illustrates processing (external processing) on the display system side (such as the display 106 side) of the X-ray diagnostic apparatus 1. The following describes an example of the pseudo gradation processing performed by the conversion function 109c, using FIG. 5. FIG. 5 is a diagram for explaining the pseudo gradation processing according to the first embodiment. The left diagram of FIG. 5 illustrates a part of the gradation of the display 106. For convenience of explanation, FIG. 5 illustrates colors of "four levels" out of "256 levels". Actually, however, the following description applies to all the "256 levels".

For example, the "10-bits" first X-ray image generated by the image generation function 109b is represented at 1024 levels (of black-and-white density). When the first X-ray image is converted into the "8-bits" image by the color reduction LUT for display, the first X-ray image is reduced in the number of colors to have the gradation of 256 levels. In other words, the original gradation information is reduced to a "quarter". Hence, in this case, the correspondence information uses the display patterns for representing the "1024 levels" using the 256 levels. For example, as illustrated in FIG. 5, the memory circuitry 108 stores in advance the display patterns in each of which four display patterns are associated with "four levels (four colors)" of the first X-ray image that is reduced in the number of colors to have the gradation of the display 106 of "one level (one color)". The display patterns illustrated in FIG. 5 are represented by the gradation of the display 106, and consequently, use each four pixels to express four times the amount of the gradation information. By using such display patterns to convert the gradation information of the first X-ray image, the original gradation information can be expressed using the gradation of the display 106. The conversion function 109c converts each of pixels of the first X-ray image into the display pattern corresponding to the color of the pixel with reference to the correspondence information stored in the memory circuitry 108.

The description has been given with reference to FIG. 5 by way of the exemplary case where four times the number of the pixels are used to express the information of "1024 colors" using "256 colors". The embodiments are, however, not limited to this example. In other words, according to the gradation of the display 106 and the gradation of the first X-ray image, the correspondence information associating these gradations with each other is generated and stored in the memory circuitry 108. For example, the memory circuitry 108 stores the correspondence information on the display pattern that uses 16 times the number of the pixels to express the information of "4096 colors" using "256 colors". The conversion function 109c selects the correspondence information to be used based on the gradation of the first X-ray image and the gradation of the display 106 serving as the display destination, and uses the selected correspondence information to perform the conversion processing.

First, the conversion function 109c acquires, from the memory circuitry 108, the correspondence information that associates each level of the first gradation with the display pattern of a plurality of pixels in the display 106 displayed with the second gradation. Each level of the first gradation refers to, for example, each level of the "1024 levels" in the first X-ray image. As illustrated in the right diagram of FIG. 5, the display pattern refers to one that represents each level of the gradation of the original X-ray image using the gradation of the display 106 illustrated in the left diagram of FIG. 5. Hereinafter, the processing to convert each level of the first gradation into the corresponding display pattern using the correspondence information will also be referred to as dithering.

That is, the conversion function 109c can represent the gradation of each of the pixels of the first X-ray image using the gradation displayed by each of the pixels of the display 106 by the dithering. For example, the conversion function 109c can use the colors of "256 levels" of the "8-bits" gradation displayed by the display 106 to express the colors of "1024 levels" of the "10-bits" gradation contained in each of the pixels of the first X-ray image. In other words, by performing the dithering, the conversion function 109c can express, for example, the first X-ray image having the "10-bits" gradation with the "8-bits" gradation.

The X-ray image with pixels each converted into "1024 kinds" of patterns is displayed on the display 106 by the display control function 109d. The "1024 kinds" of patterns are recognized as "1024 levels" of colors due to a visual effect occurring when the operator views the image. In other words, the X-ray image viewed by the operator is actually an "8-bits" image displayed by the display 106, but is recognized as a "10-bits" image due to the visual effect.

Consequently, by performing the dithering, the conversion function 109c can express intermediate colors of gradation in a pseudo manner. The conversion function 109c can express, for example, the "10-bits" gradation information contained in each of the pixels of the first X-ray image on the "8-bits" display 106 by increasing the apparent gradation levels in a pseudo manner by performing the dithering. Hereinafter, the X-ray image expressing the "10-bits" X-ray image with "8-bits" by the dithering will be referred to as a "pseudo 10-bits" X-ray image.

The X-ray image converted into the "pseudo 10-bits" X-ray image is already an "8-bits" image from the viewpoint of each pixel. Consequently, the X-ray image having been subjected to the pseudo gradation processing is not reduced in the number of colors with the color reduction LUT for display included in the display 106, and can be displayed on the display 106 while containing information corresponding to the "10-bits" gradation information. The "pseudo 10-bits" X-ray image having been subjected to the pseudo gradation processing and the "10-bits" X-ray image before being subjected to the pseudo gradation processing are stored in the memory circuitry 108.

In the above example, the case has been described where the conversion function 109c expresses the colors of "256 levels" as the colors of "1024 levels" by performing the dithering to express each of the pixels of the first X-ray image with four pixels. The embodiments are, however, not limited to this example. For example, the conversion function 109c can express the colors of "256 levels" as colors of "2304 levels" by performing the dithering to express each of the pixels of the first X-ray image with nine pixels of "3×3".

For example, the conversion function 109c can also express the colors of "256 levels" as colors of "4096 levels" by performing the dithering to express each of the pixels of the first X-ray image with 16 pixels of "4×4".

Figure 6A:
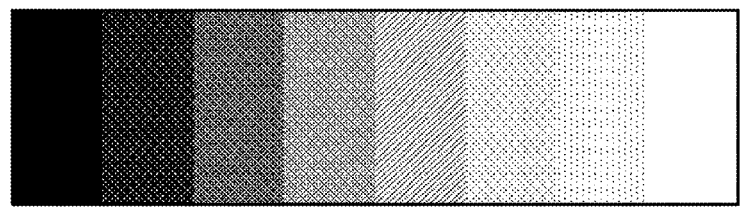
FIG. 6A is a diagram for explaining the pseudo gradation processing according to the first embodiment.
Figure 6B:
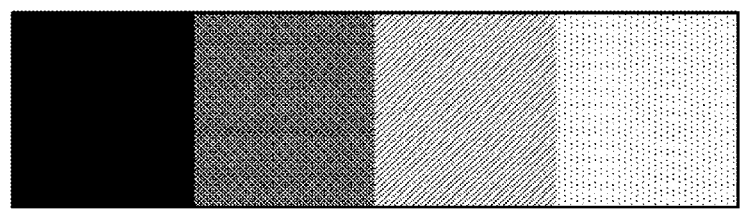
FIG. 6B is a diagram for explaining the pseudo gradation processing according to the first embodiment.
Figure 6C:
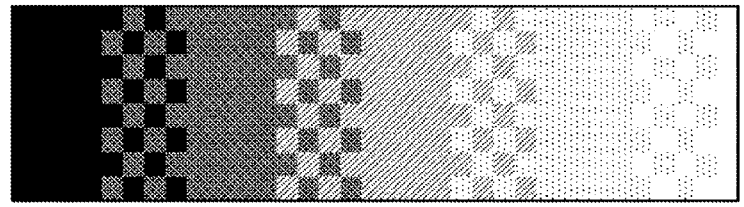
FIG. 6C is a diagram for explaining the pseudo gradation processing according to the first embodiment.

As described above, the conversion function 109c increases the number of gradation levels in a pseudo manner by performing the pseudo gradation processing, and thereby can prevent the information contained in the original data from being lost. Furthermore, the conversion function 109c can reduce stepwise noise by performing the pseudo gradation processing. The following describes the reduction of the stepwise noise by performing the pseudo gradation processing, using FIGS. 6A, 6B, and 6C. FIGS. 6A, 6B, and 6C are diagrams for explaining the pseudo gradation processing according to the first embodiment. If the original data of colors of "eight levels" illustrated in FIG. 6A is displayed on the display 106 without being subjected to the pseudo gradation processing, the display 106 displays an image in which colors has been reduced to colors of "four levels" by simple color reduction in the color reduction LUT for display, as illustrated in FIG. 6B. If, instead, the original data of colors of "eight levels" illustrated in FIG. 6A is displayed on the display 106 after being subjected to the pseudo gradation processing as illustrated in FIG. 6C, the image displayed is the same in being displayed in colors of "four levels", but can be displayed as a smooth image as a whole because expressing the intermediate colors using the display patterns reduces the stepwise noise.

Figure 7:
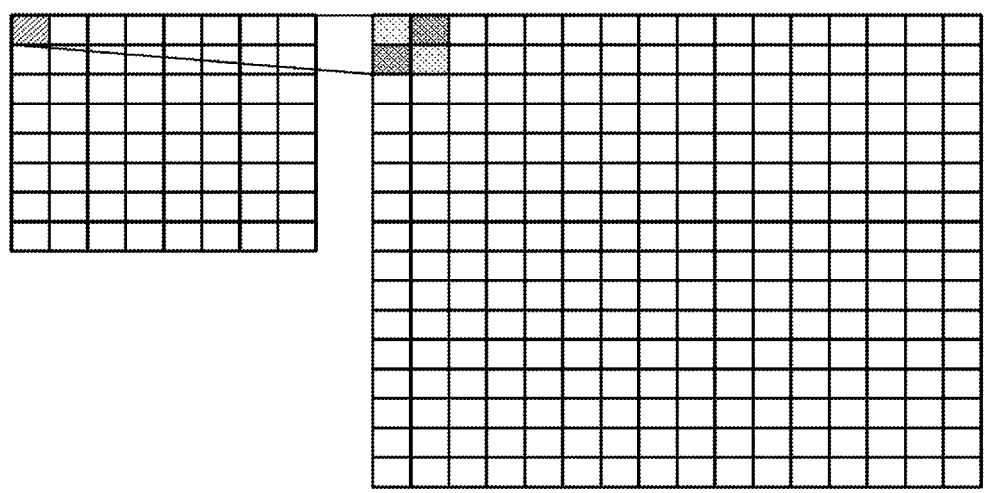
FIG. 7 is a diagram for explaining the pseudo gradation processing according to the first embodiment.

As described above, the dithering performed by the conversion function 109c is processing to convert the gradation of each of the pixels of the first X-ray image into the display pattern that is a combination of colors of a plurality of pixels. Consequently, performing the dithering involves an increase in the number of pixels of the X-ray image, as illustrated in FIG. 7. FIG. 7 is a diagram for explaining the pseudo gradation processing according to the first embodiment. For example, if the dithering is performed to express "one pixel" of the X-ray image illustrated in the left diagram of FIG. 7 by "four pixels" of "2×2" illustrated in the right diagram of FIG. 7, the number of pixels of the X-ray image subjected to the dithering increases to four times that of the original image.

In some cases, depending on the number of pixels included in the X-ray image, the effect of increasing the apparent number of gradation levels caused by the dithering may fail to be obtained. In other words, since the dithering is processing to express each of the pixels of the first X-ray image with a plurality of pixels on the display 106, each of the pixels of the first X-ray may fail to be displayed using the pixels on the display 106, and thus, the visual effect by the dithering may fail to be obtained, in some cases depending on the number of pixels of the first X-ray image relative to the number of pixels of the display 106.

Hence, before performing the pseudo gradation processing, the conversion function 109c determines whether to perform the pseudo gradation processing. First, the conversion function 109c assumes to perform the pseudo gradation processing to convert, for example, the first X-ray image with the number of pixels of "512×512" and the number of gradation levels of "10-bits" into an X-ray image with the number of pixels of "1024×1024" and the number of gradation levels of "pseudo 10-bits". If, for example, the overall number of pixels of the display 106 is "512×512", "four pixels" in the X-ray image after the conversion ("one pixel" in the first X-ray image before the conversion) are assumed to be expressed by "one pixel" on the display 106. In this case, the X-ray image after the dithering cannot be displayed on the display 106, and consequently, the conversion function 109c determines, in the determination processing, not to perform the pseudo gradation processing.

If, instead, the display 106 is, for example, a large-screen monitor or a high-resolution monitor and can display the X-ray image after the pseudo gradation processing, the X-ray image can be displayed on the display 106 even if the number of pixels of the X-ray image is increased by the dithering. Therefore, if the number of pixels of the display 106 is sufficiently large, the conversion function 109c determines, in the determination processing, that the X-ray image with the interpolated number of gradation levels can be displayed, and performs the pseudo gradation processing. In other words, the conversion function 109c determines, in the determination processing, whether the X-ray image with the interpolated number of gradation levels can be displayed in view of the relation between the number of pixels of the display 106 and the number of pixels of the X-ray image, and if it can be displayed, performs the pseudo gradation processing. If, in the determination processing, the pseudo gradation processing is determined not necessary to be performed, such as in the case where the number of gradation levels of the first X-ray image is smaller than the number of gradation levels displayed by the display 106, the conversion function 109c determines not to perform the pseudo gradation processing.

Figure 8:
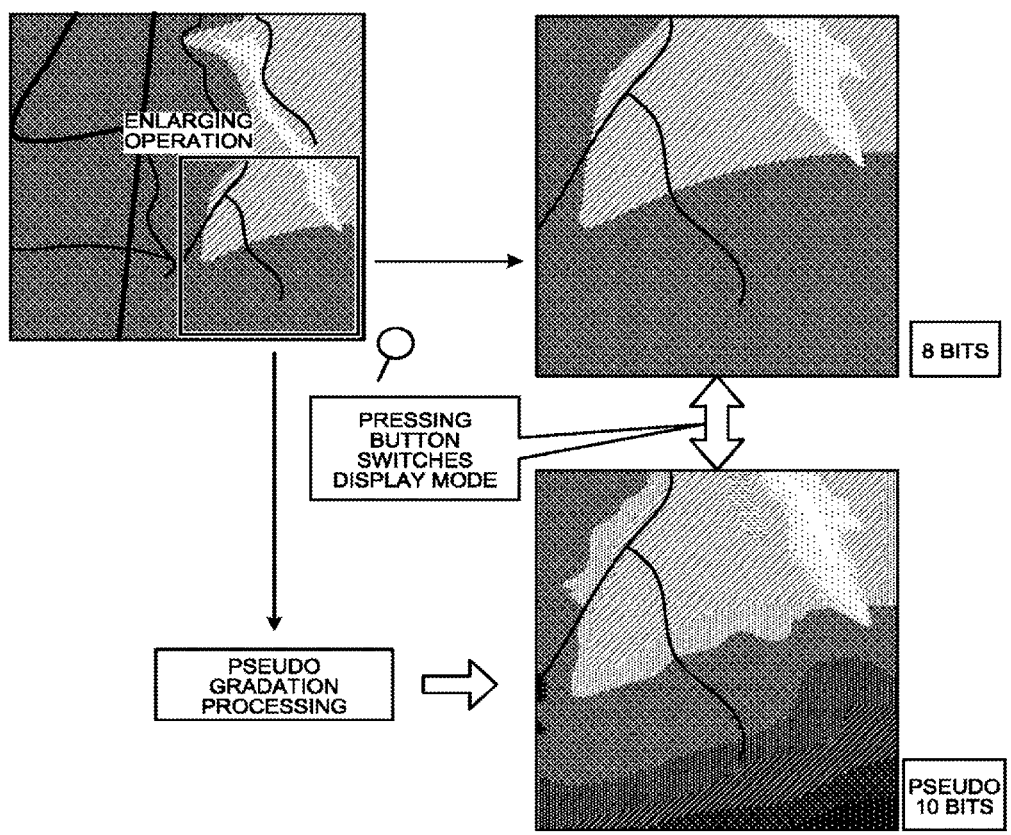
FIG. 8 is a diagram for explaining a gradation interpolation mode according to the first embodiment.

If the X-ray image to be displayed on the display 106 by the display control function 109d is not the entire X-ray image generated by the image generation function 109b, but the partial region of the X-ray image, the conversion function 109c performs the determination processing for the partial region of the X-ray image, and performs the pseudo gradation processing on the pixels included in the partial region of the X-ray image. For example, in the case of displaying only an enlarged image of the partial region of the entire X-ray image, the conversion function 109c can determine, based on the relation between the number of pixels corresponding to the partial region to be displayed and the number of pixels of the display 106, whether the X-ray image with the interpolated number of gradation levels can be displayed. The following describes the pseudo gradation processing involving the enlargement display of the X-ray image, using FIG. 8. FIG. 8 is a diagram for explaining a gradation interpolation mode according to the first embodiment.

For example, as illustrated in the upper left diagram of FIG. 8, the display control function 109d first displays the entire X-ray image not having been subjected to the pseudo gradation processing on the display 106. In other words, the display control function 109d displays, on the display 106, the X-ray image acquired by replacing each level of the first gradation of each of the pixels in the first X-ray image with a corresponding level in the second gradation.

Then, the reception function 109f receives, from the operator, an operation to the X-ray image that has been acquired by replacing each level of the first gradation of each of the pixels in the first X-ray image with the corresponding level in the second gradation and displayed on the display 106. For example, the reception function 109f receives a specification of the partial region of the entire X-ray image to be enlarged and displayed from the operator who has referred to the X-ray image illustrated in the upper left diagram of FIG. 8. As an example, the reception function 109f receives the rectangular region illustrated in the upper left diagram of FIG. 8 that is adjusted as the partial region to be enlarged and displayed, through operation of the mouse included in the input circuitry 107.

Then, the region specification function 109e specifies the partial region in the first X-ray image based on the operation received by the reception function 109f. For example, if the operator has performed the operation to specify the rectangular region illustrated in the upper left diagram of FIG. 8, the region specification function 109e specifies the rectangular region illustrated in the upper left diagram of FIG. 8 as the partial region in the first X-ray image.

The conversion function 109c determines whether the partial region of the entire X-ray image that has been subjected to the enlarging operation can be displayed on the display 106 after being subjected to the pseudo gradation processing. If having determined that the partial region having been subjected to the enlarging operation can be displayed on the display 106, the conversion function 109c converts each level of the first gradation of each of the pixels included in the partial region into the display pattern based on the correspondence information. In other words, the conversion function 109c performs the pseudo gradation processing on the specified partial region to convert the X-ray image into the "pseudo 10-bits" X-ray image.

Then, the image generation function 109b generates an X-ray image (hereinafter, also referred to as a second X-ray image) that expresses a plurality of pixels included in the partial region as the display patterns converted by the conversion function 109c. For example, the image generation function 109b generates the "pseudo 10-bits" second X-ray image from the "10-bits" first X-ray image. The second X-ray image may be an image corresponding to only the partial region of the first X-ray image, or may be an image corresponding to a region of the X-ray image including the partial region. The second X-ray image is an example of a second image described in the claims.

The display control function 109d displays the second X-ray image generated by the image generation function 109b on the display 106, as illustrated in the lower right diagram of FIG. 8. In other words, the display control function 109d displays the "pseudo 10-bits" X-ray image on the display 106. In FIG. 8, the second X-ray image is the image corresponding to only the partial region of the first X-ray image.

If the number of pixels of the display 106 is insufficient, or if the pseudo gradation processing is set to not be performed, the conversion function 109c does not perform the pseudo gradation processing on the region of the entire X-ray image that has been subjected to the enlarging operation, and the display control function 109d enlarges and displays the "8-bits" X-ray image as illustrated in the upper right diagram of FIG. 8. Hereinafter, the mode of displaying the X-ray image having been subjected to the pseudo gradation processing (that is, the mode of displaying the second X-ray image) will be referred to as a gradation interpolation mode, and the mode of displaying the X-ray image not subjected to the pseudo gradation processing will be referred to as a normal mode.

Hereinafter, the X-ray image displayed in the normal mode on the display 106 by the display control function 109d will also be referred to as a third X-ray image. For example, the X-ray image illustrated in the upper right diagram of FIG. 8 is the third X-ray image. The third X-ray image may be an image corresponding to only the partial region of the first X-ray image, or may be an image corresponding to a region of the X-ray image including the partial region. The third X-ray image in FIG. 8 is the image corresponding to only the partial region of the first X-ray image. The third X-ray image is an example of a third image described in the claims.

As an example, as illustrated in the lower right diagram of FIG. 8, in the case where the part of the X-ray image is enlarged and displayed, the conversion function 109c automatically switches the display mode to the gradation interpolation mode, and the display control function 109d displays the "pseudo 10-bits" X-ray image on the display 106. A case may exist where the switching between the normal mode and the gradation interpolation mode is automatically performed, or performed by the operator. For example, pressing a button included in the input circuitry 107 can cause the display control function 109d to switch the display mode of the image.

The following more specifically describes the pseudo gradation processing involving the enlarging operation of the X-ray image. The following describes, as an example, a case where the total number of pixels of the display 106 is "512×512", and the total the number of pixels of the first X-ray image generated by the image generation function 109b is "512×512". For example, in the upper left diagram of FIG. 8, the display 106 displays the entire first X-ray image, and "one pixel" of the display 106 displays "one pixel" of the first X-ray image. The following also describes, as an example, a case where the display control function 109d enlarges by "twice" and displays the specified partial region of the entire first X-ray image on the display 106. For example, in the upper right diagram of FIG. 8, the display 106 displays a "quarter" region of the entire first X-ray image, and "four pixels" of "2×2" of the display 106 displays "one pixel" of the first X-ray image.

For example, the conversion function 109c first performs the pseudo gradation processing on the partial region of the entire X-ray image illustrated in the upper left diagram of FIG. 8 specified by the operator. For example, the conversion function 109c performs the pseudo gradation processing to express "one pixel" in the first X-ray image by the "four pixels" of "2×2". Then, the image generation function 109b generates the second X-ray image that expresses the pixels included in the partial region of the X-ray image illustrated in the upper left diagram of FIG. 8 as the display patterns converted by the pseudo gradation processing. Then, the display control function 109d displays the second X-ray image generated by the image generation function 109b on the display 106, as illustrated in the lower right diagram of FIG. 8.

As described above, in the case where the part of the entire X-ray image having been subjected to the enlarging operation is displayed, the number of pixels of the displayed X-ray image is reduced relative to the number of pixels of the display 106, and consequently, room is provided for displaying the X-ray image after being subjected to the dithering on the display 106. Consequently, even if, for example, the entire X-ray image having been subjected to the dithering cannot be displayed due to a limit of the number of pixels of the display 106 (such as a case where the number of pixels of the X-ray image is large or a case where the number of pixels of the display 106 is small), the X-ray image having been subjected to the dithering can be displayed by enlarging and displaying the partial region of the X-ray image.

The conversion function 109c can determine the content of the pseudo gradation processing in view of the relation between the number of pixels of the display 106 and the number of pixels of the displayed X-ray image. For example, even if the number of gradation levels of the original data is larger than "10-bits" levels, the display control function 109d can display the X-ray image in the gradation interpolation mode by adjusting the ratio of enlargement of the X-ray image. The case has been described with reference to FIG. 8 where, in the case of enlarging by "twice" (display magnification for displaying the "quarter" region of the entire first X-ray image) and displaying the specified partial region of the entire X-ray image on the display 106, the conversion function 109c performs the pseudo gradation processing to express "one pixel" of the first X-ray image using "four pixels" on the display 106. In the case of enlarging by "four times" (display magnification for displaying "one-sixteenth" region of the entire first X-ray image) and displaying a specified partial region of the entire X-ray image on the display 106, the conversion function 109c can perform the pseudo gradation processing to express "one pixel" of the first X-ray image using "16 pixels" of "4×4" on the display 106. In other words, in the case of displaying a "12-bits" X-ray image on the "8-bits" display 106, the conversion function 109c converts the X-ray image from the "12-bits" X-ray image to a "pseudo 12-bits" X-ray image by performing the pseudo gradation processing to express "one pixel" in the first X-ray image by the "16 pixels" on the display 106. The display control function 109d enlarges by "four times" and displays the part of the X-ray image on the display 106, and displays the "pseudo 12-bits" X-ray image.

Figure 9:
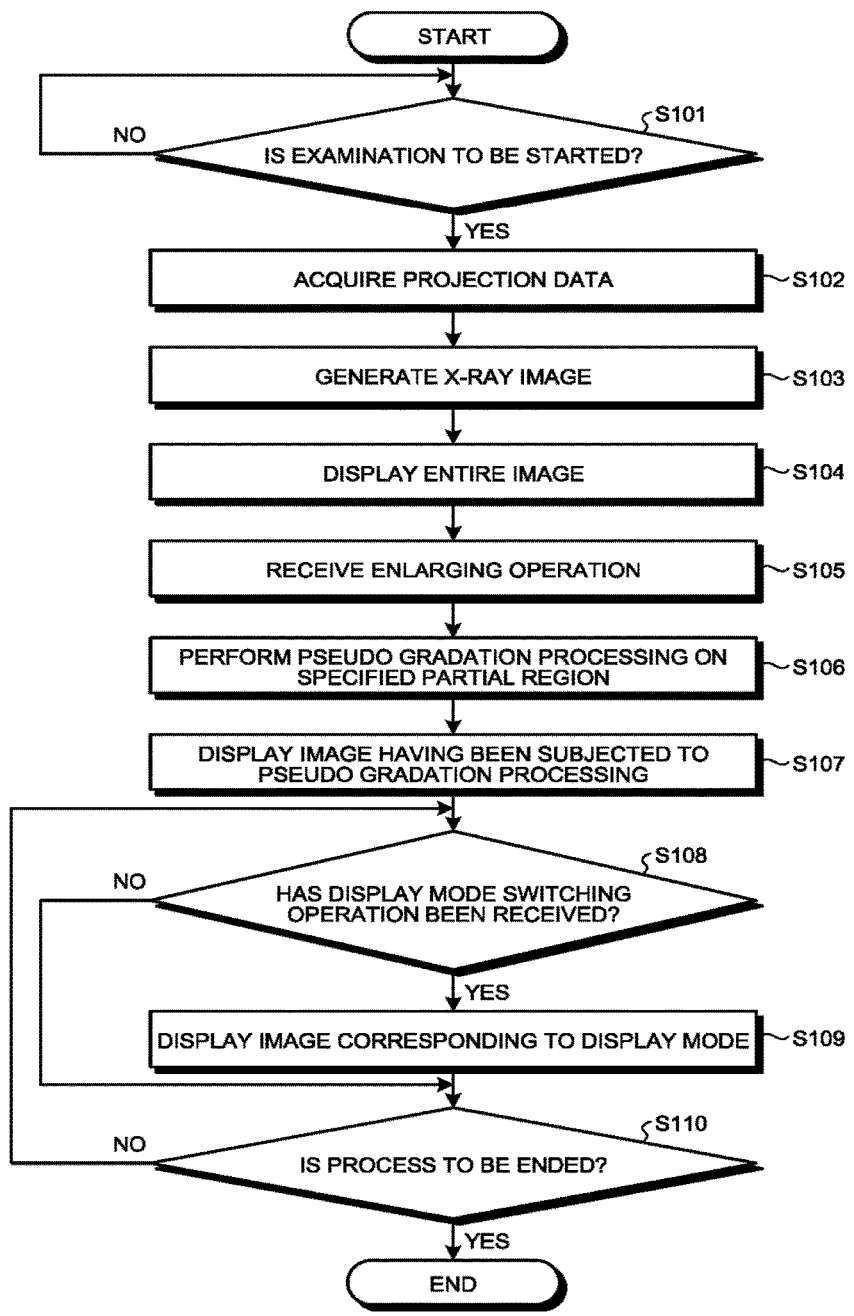
FIG. 9 is a flowchart for explaining a sequence of processing of the X-ray diagnostic apparatus according to the first embodiment.

The following describes an exemplary procedure of the processing performed by the X-ray diagnostic apparatus 1, using FIG. 9. FIG. 9 is a flowchart for explaining the sequence of the processing of the X-ray diagnostic apparatus 1 according to the first embodiment. Steps S101, S102, and S110 are steps corresponding to the control function 109a. Step S103 is a step corresponding to the image generation function 109b. Step S106 is a step corresponding to the conversion function 109c and the image generation function 109b. Steps S104, S107, S108, and S109 are steps corresponding to the display control function 109d. Step S105 is a step corresponding to the region specification function 109e and the reception function 109f.

First, the processing circuitry 109 determines whether an examination start request has been received from the operator (Step S101). If not (No at Step S101), the processing circuitry 109 is placed in a waiting state. If so (Yes at Step S101), the processing circuitry 109 acquires projection data of the subject P (Step S102), and generates the X-ray image based on the signals acquired from the subject P (Step S103). Then, the processing circuitry 109 displays the entire generated X-ray image on the display 106 (Step S104), receives the enlarging operation from the operator, and specifies the partial region in the first X-ray image (Step S105). The processing circuitry 109 performs the pseudo gradation processing on the specified partial region of the entire X-ray image to generate the second X-ray image (Step S106). The processing circuitry 109 displays the X-ray image (second X-ray image) having been subjected to the pseudo gradation processing on the display 106 (Step S107).

The processing circuitry 109 determines whether the switching operation of the display mode has been received (Step S108). If so (Yes at Step S108), the processing circuitry 109 displays the X-ray image having been subjected to the pseudo gradation processing or the X-ray image not having been subjected to the pseudo gradation processing, depending on the content of the operation, on the display 106 (Step S109). If not (No at Step S108), the processing circuitry 109 determines whether an end command has been received from the operator (Step S110). If not (No at Step S110), the processing circuitry 109 performs the processing of Step S108 again. If so (Yes at Step S110), the processing circuitry 109 ends the process.

A case may exist where, at Step S107, the processing circuitry 109 displays the X-ray image not having been subjected to the pseudo gradation processing on the display 106. The case has been described where the pseudo gradation processing is performed on the partial region having been subjected to the enlarging operation at Step S106. However, a case may exist where the pseudo gradation processing is performed on the entire first X-ray image in advance, and then, the second X-ray image is generated according to the partial region of the entire first X-ray image that has been subjected to the enlarging operation. The processing circuitry 109 may determine, prior to the pseudo gradation processing at Step S106, whether the X-ray image having been subjected to the pseudo gradation processing can be displayed on the display 106.

As describe above, according to the first embodiment, the image generation function 109b generates the first X-ray image in which each of the pixels is expressed with the first gradation based on the X-rays transmitted through the subject P. The region specification function 109e specifies the partial region in the first X-ray image. The conversion function 109c converts the level in the first gradation of each of the pixels included in the partial region in the first X-ray image into the corresponding display pattern based on the correspondence information that associates each level of the first gradation with the display pattern of a plurality of pixels in the display 106 displayed with the second gradation having fewer levels than the first gradation. The image generation function 109b generates the second X-ray image that expresses the pixels included in the partial region of the first X-ray image as the display patterns converted by the conversion function 109c. The display control function 109d displays the second X-ray image generated by the image generation function 109b on the display 106. Consequently, the X-ray diagnostic apparatus 1 according to the first embodiment presents, to the operator, the information that will be lost if the simple color reduction is performed in the display 106, and thus can improve the accuracy of the examinations using the X-ray image.

As described above, the display control function 109d according to the first embodiment can display the X-ray image having been subjected to the pseudo gradation processing on the display 106 that is a color monitor configured to display the image with the gradation of "8-bits (256 gradation levels)" for each of the RGB colors. Consequently, even in the case of displaying the X-ray image using an "8-bits" color monitor that has come to be used in recent years for displaying the X-ray image because of reduction in price and increase in resolution, the X-ray diagnostic apparatus 1 according to the first embodiment can improve the accuracy of the examinations using the X-ray image by presenting, to the operator, the gradation information contained in the X-ray image having, for example, the "10-bits" gradation or the "12-bits" gradation.

As described above, the conversion function 109c according to the first embodiment performs the pseudo gradation processing on the X-ray image, and the display control function 109d displays the X-ray image having been subjected to the pseudo gradation processing on the display 106. Consequently, the X-ray diagnostic apparatus 1 according to the first embodiment can improve the accuracy of the examinations using the X-ray image by reducing the step-wise noise from the X-ray image displayed on the display 106 and thus presenting the X-ray image improved in overall visual quality to the operator.

As described above, the conversion function 109c according to the first embodiment performs the pseudo gradation processing on the X-ray image before being subjected to the simple color reduction using the color reduction LUT for display in the monitor. Consequently, unlike, for example, antialiasing that reduces the resolution by blurring the boundaries of the X-ray image having been subjected to the simple color reduction, the X-ray diagnostic apparatus 1 according to the first embodiment displays the X-ray image effectively using the gradation information that has been contained in the image data before being reduced in the number of colors, and thus can improve the accuracy of the examinations.

As described above, the conversion function 109c according to the first embodiment performs the determination processing, and depending on the result thereof, performs the pseudo gradation processing on the X-ray image. Consequently, for example, if, due to the relation with the number of pixels of the display 106, the effect of the gradation interpolation by the dithering is not obtained by displaying the X-ray image having been subjected to the pseudo gradation processing on the display 106, the X-ray diagnostic apparatus 1 according to the first embodiment does not perform the dithering, and thus can reduce computational load.

As described above, the display control function 109d according to the first embodiment enlarges and displays the X-ray image having been subjected to the pseudo gradation processing on the display 106. Consequently, the X-ray diagnostic apparatus 1 according to the first embodiment presents the X-ray image having been subjected to the pseudo gradation processing to the operator not only in the case where the display 106 is a high-resolution monitor or a large-screen monitor, and thus can improve the accuracy of the examinations using the X-ray image.

As described above, the display control function 109d according to the first embodiment enlarges and displays the X-ray image having been subjected to the pseudo gradation processing on the display 106. Consequently, even if the gradation of the X-ray image is a multi-gradation, such as a "12-bits" gradation or a "14-bits" gradation, the X-ray diagnostic apparatus 1 according to the first embodiment can improve the accuracy of the examinations using the X-ray image, by determining the content of the dithering and the display magnification in view of the relation with the number of pixels of the display 106, and by presenting the X-ray image having been subjected to the dithering that can obtain the effect of the gradation interpolation to the maximum extent.

As described above, the display control function 109d according to the first embodiment can switch between the gradation interpolation mode of displaying the X-ray image having been subjected to the pseudo gradation processing and the normal mode of displaying the X-ray image not having been subjected to the pseudo gradation processing. Consequently, the X-ray diagnostic apparatus 1 according to the first embodiment allows display and comparison to be performed using the original image data in a conventional way, and further allows the display and the comparison to be performed using the X-ray image with interpolated gradation levels, thus being capable of improving the accuracy of the examinations.

The case has been described with reference to FIG. 8 where the display control function 109d displays the specified partial region on the entire display 106. The embodiments are, however, not limited to this case. For example, a case may exist where the display control function 109d displays the entire X-ray image on the display 106, and in addition, enlarges a region surrounded by an icon (such as a "magnifier" tool) movable over the X-ray image, and displays the region so as to overlap it with a part of the entire X-ray image. The display control function 109d can display, for example, the partial region of the X-ray image having been subjected to the pseudo gradation processing in a part of the entire X-ray image not having been subjected to the pseudo gradation processing.

The case has been described with reference to FIG. 8 where the region specification function 109e specifies the partial region in the first X-ray image based on the operation received by the reception function 109f. The embodiments are, however, not limited to this case. The following describes other examples of the specification of the partial region by the region specification function 109e.

First, a case will be described where the first X-ray image includes a device, and the partial region is specified based on information on the device in the first X-ray image. For example, after the image generation function 109b has generated the first X-ray image, the ROI setting function 109g sets a region of interest (hereinafter, abbreviated as ROI) that includes the device in the first X-ray image. The ROI may be a region along the outline of the device, or may be a rectangular region or a region having another shape including the device.

Setting of the ROI will be described by way of an exemplary case where the device included in the first X-ray image is a stent. The stent is, for example, a metal mesh, and is indwelled in a narrow portion in a blood vessel of the subject P to be used for reducing the restenosis rate of the narrow portion in an interventional treatment.

The ROI setting function 109g sets the ROI, for example, based on stent markers indicating the position of the stent. The stent markers are made of, for example, a radiopaque metal. For example, in the interventional treatment to the narrow portion using a balloon-bearing catheter, the stent markers are attached to two places of the balloon portion. In this case, the stent is inserted into the subject in a state tightly attached to the outside of the balloon portion of the balloon-bearing catheter, and as a result, the stent markers virtually indicate the position of the stent. The catheter is a tube for medical use. For example, in the interventional treatment, the balloon portion of the balloon-bearing catheter is inserted up to the narrow portion, and a liquid is injected into the balloon through the catheter. As a result, the balloon is expanded, and the narrow portion is expanded.

The stent markers are expressed more clearly than body tissue of the subject P and the stent in the first X-ray image. Consequently, even if the position of the stent cannot be directly identified from the first X-ray image, the ROI setting function 109g can identify the position of the stent based on the stent markers. Hereinafter, points, such as the stent markers included in the first X-ray image, used for identifying the position of the device in the first X-ray image will also be referred to as feature points.

The shape and size of the ROI based on the positions of the stent markers may be set using information on the shape and size of the stent, or preset settings may be used. A case may exist where the ROI setting function 109g sets the ROI based on the image of the device in the first X-ray image without using the feature points, such as the stent markers.

Then, the region specification function 109e determines, according to the information on the device included in the ROI, whether to specify the ROI as the partial region. The information on the device may be information acquired from the first X-ray image, or may be information input by the operator. Regarding the determination as to whether to specify the ROI as the partial region, the following describes, as an example, a case where the device included in the first X-ray image is the stent.

For example, the region specification function 109e first acquires information on the stent based on the image of the stent in the first X-ray image. The information on the stent is information on the configuration of the stent, such as the mesh density of the stent. For example, the region specification function 109e acquires the thickness or the interspace of line-shaped metal constituting the mesh as the information on the stent from the image of the stent.

If the mesh of the stent is fine (for example, if the line-shaped metal constituting the mesh is thin, or if the interspace thereof is small), the contrast of the stent in the first X-ray image is low. If the first X-ray image including such a stent is subjected to the color reduction using the color reduction LUT for display in the monitor, the stent is expressed at fewer gradation levels, and is reduced in visibility.

Hence, if the mesh of the stent is fine, the region specification function 109e specifies the ROI including the stent in the partial region to be dithered. For example, the region specification function 109e calculates a value (such as the thickness or the interspace of the metal constituting the mesh) representing the mesh density of the stent based on the image of the stent in the first X-ray image, and compares the calculated value with a threshold to determine whether to specify the ROI as the partial region.

Alternatively, the region specification function 109e calculates the contrast (faintness) of the image of the stent in the first X-ray image, and determines, based on the calculated contrast, whether to specify the ROI as the partial region. For example, the region specification function 109e calculates the ratio or the difference between the maximum value and the minimum value of pixel values in the image of the stent, and compares the calculated value with a threshold to determine whether to specify the ROI as the partial region.

The contrast of the image in the ROI or the contrast of an image including the image of the stent in the ROI may be calculated as the contrast of the image of the stent. For example, if the ROI is a rectangular region including the stent, the region specification function 109e can calculate the contrast of a region along the outline of the stent.

If a plurality of such first X-ray images, such as fluoroscopic images used in the interventional treatment, are acquired along time, the contrast of the image of the stent may vary in some cases due to a variation in angle of X-ray irradiation, distribution of a contrast agent, or position of the stent, even if the images have been acquired from the same subject P and the same stent. In such a case, the region specification function 109e may calculate the contrast for determining whether to specify the ROI as the partial region on an image-by-image basis, or may calculate one contrast value for the images. For example, the region specification function 109e calculates the contrast of the image of the stent in each of the first X-ray images, and determines whether to specify the ROI as the partial region on an image-by-image basis. Alternatively, for example, based on the contrast of the image of the stent in the first image of the first X-ray images acquired along time, or based on the average value of contrast values of the images of the stent in the respective first X-ray images, the region specification function 109e determines, for all the images, whether to specify the ROI in each of the first X-ray images in the partial region.

A case may exist where the region specification function 109e determines, based on the information on the stent input by the operator, whether to specify the ROI as the partial region. For example, information specifying whether to specify the stent in the partial region is first stored in the memory circuitry 108 for each stent (for example, for each standard or product name of the stent), or for each value representing the mesh density. The region specification function 109e or the operator may set such information.

Then, the input circuitry 107 receives an input operation of the information on the stent from the operator. The information on the stent received via the input operation may be the standard or the product name of the stent, or may be the value representing the mesh density. The region specification function 109e compares the information specifying whether to specify the stent in the partial region with the input information on the stent to determine whether to specify the ROI as the partial region.

If the ROI is specified as the partial region, the conversion function 109c converts the level in the first gradation of each of the pixels included in the ROI into the corresponding display pattern, and the image generation function 109b generates the second X-ray image that expresses the pixels included in the ROI of the first X-ray image as the display patterns. The second X-ray image may be an image corresponding to only the ROI, or may be an image corresponding to a part or all of the first X-ray image including the ROI.

That is, each of the pixels included in the ROI is converted into the display pattern, and the number of pixels increases. Consequently, a plurality of pixels in the second X-ray image are displayed by one pixel of the display 106, and the visual effect of the gradation interpolation caused by the dithering may fail to be obtained in some cases. In such cases, the image generation function 109b generates the second X-ray image as an image corresponding to only the ROI, or as an image corresponding to a part of the first X-ray image including the ROI. As a result, the number of pixels in the second X-ray image is reduced, and the visual effect of the gradation interpolation caused by the dithering can be obtained when the second X-ray image is displayed on the display 106. If the display 106 is, for example, a large-screen monitor or a high-resolution monitor, the image generation function 109b can obtain the visual effect of the gradation interpolation caused by the dithering when the second X-ray image is displayed on the display 106 even if the image generation function 109b generates the second X-ray image as an image corresponding to the entire first X-ray image.

The following describes a case where the ROI is set in the first X-ray image regardless of whether the first X-ray image includes the device. For example, the ROI setting function 109g may set the ROI based on the operation received from the operator by the reception function 109f, or may set an area (such as an area located at the center of the first X-ray image and having a predetermined shape and size) set in advance as the ROI.

After the ROI is set, the region specification function 109e determines, according to whether the ROI includes the device, whether to specify the ROI as the partial region. Regarding the determination as to whether to specify the ROI as the partial region, the following describes, as an example, a case where the first X-ray image is a fluoroscopic image used in the interventional treatment, and a doctor who performs procedures using the catheter is referring to the fluoroscopic image.

If the ROI includes the catheter, the doctor referring to the fluoroscopic image focuses his or her attention mainly on the catheter. The catheter is clearly expressed with a sufficient contrast in the first X-ray image, so that the doctor can sufficiently view the catheter without the help of dithering.

Consequently, if the ROI includes the catheter, the region specification function 109e does not specify the ROI as the partial region.

If, instead, the ROI does not include the catheter, the doctor focuses his or her attention, for example, on the body tissue of the subject P. The body tissue in the first X-ray image has a lower contrast than that of the catheter. If the first X-ray image is subjected to the color reduction using the color reduction LUT for display in the monitor, the body tissue is expressed at fewer gradation levels, and is reduced in visibility. Therefore, if the ROI does not include the catheter, the region specification function 109e specifies the ROI as the partial region.

Although the above has been described by exemplifying the catheter, the region specification function 109e can determine, according to whether a line-shaped device other than the catheter is included, whether to specify the ROI as the partial region. The line-shaped device is a device that is expressed in the first X-ray image at a contrast at which the device is visible without the help of dithering, and examples thereof other than the catheter include, but are not limited to, a guide wire, a puncture needle, and a transesophageal echocardiography (TEE) probe.

If the ROI is specified as the partial region, the conversion function 109c converts the level in the first gradation of each of the pixels included in the ROI into the corresponding display pattern, and the image generation function 109b generates the second X-ray image that expresses the pixels included in the ROI of the first X-ray image as the display patterns. The second X-ray image may be an image corresponding to only the ROI, or may be an image corresponding to a part or all of the first X-ray image including the ROI. The second X-ray image may be an image that expresses each of the pixels included in the ROI as the display pattern, or may be an image that expresses each plurality of pixels included in the ROI as the display pattern.

In other words, if the increase in the number of pixels caused by the conversion of each of the pixels included in the ROI into the display pattern will prevent the visual effect of the gradation interpolation caused by the dithering from being obtained, the conversion function 109c avoids the increase in the number of pixels by converting each plurality of pixels included in the ROI into the display pattern, and thus can obtain the visual effect of the gradation interpolation caused by the dithering.

For example, if the first gradation is the "10-bits" gradation and the second gradation is the "8-bits" gradation, the conversion function 109c calculates the average value of the pixel values in the first gradation for each four pixels included in an area of "2×2" in the ROI, and converts the pixels in the area of "2×2" into a display pattern corresponding to the calculated average value. The image generation function 109b generates the second X-ray image that expresses the pixels in the area of "2×2" included in the ROI as the display pattern. In such a second X-ray image, each four pixels in the first X-ray image are expressed as one display pattern in the second X-ray image, so that spatial resolution drops, but density resolution is maintained.

The conversion function 109c may switch between whether to convert each of the pixels included in the ROI into the display pattern, or to convert each plurality of pixels included in the ROI into the display pattern depending on which of the spatial resolution and the density resolution is given a higher priority. In the case of converting each of the pixels included in the ROI into the display pattern, the image generation function 109b may generate the second X-ray image as an image corresponding to only the ROI, or as an image corresponding to a part of the first X-ray image including the ROI in order to reduce the number of pixels in the second X-ray image.

The following describes a case of specifying the partial region based on annotation information attached to the first X-ray image. The annotation information is, for example, a mark or a comment attached to a lesion part, such as a tumor, by a technician or a radiologist referring to the first X-ray image. Otherwise, the annotation information is, for example, a mark or a comment attached to the first X-ray image as a lesion part detected through a computer aided diagnosis (CAD).

For example, if the mark attached to the lesion part is a circle or a rectangle surrounding the lesion part, the region specification function 109e specifies the region surrounded by the mark as the partial region. Otherwise, the region specification function 109e specifies the partial region based on the position where the circle or the rectangle is attached. As an example, the region specification function 109e determines a pixel having a pixel value different from that of a pixel in the position where the circle or the rectangle is attached by a value equal to or smaller than a threshold to be a pixel included in the lesion part, and sequentially repeats this determination process for a pixel adjacent to the pixel determined to be the pixel included in the lesion part so as to calculate a region corresponding to the lesion part, and specifies the calculated region as the partial region.

If the partial region has been specified based on the annotation information, the conversion function 109c converts the level in the first gradation of each of the pixels included in the partial region into the corresponding display pattern, and the image generation function 109b generates the second X-ray image that expresses the pixels included in the partial region of the first X-ray image as the display patterns. The second X-ray image may be an image corresponding to only the partial region in the first X-ray image, or may be an image corresponding to a part or all of the first X-ray image including the partial region. The second X-ray image may be an image that expresses each of the pixels included in the ROI as the display pattern, or may be an image that expresses each plurality of pixels included in the ROI as the display pattern.

For example, if a diagnostic reading is performed using a color monitor of "8-bits (256 gradation levels)" to view a tumor in the subject P in a conference or a report system, the visibility of the tumor can be enhanced by giving a higher priority to the density resolution than to the spatial resolution by converting each plurality of pixels included in the partial region into the display pattern.

In the first embodiment described above, the case has been described where the pseudo gradation processing is applied to the specified partial region. Instead, in a second embodiment, a case will be described where the pseudo gradation processing is applied to pixels to be the same color after being subjected to the color reduction. The X-ray diagnostic apparatus 1 according to the second embodiment has the same configuration as that of the X-ray diagnostic apparatus 1 according to the first embodiment illustrated in FIG. 1, but differs therefrom in the processing in the conversion function 109c and the image generation function 109b. Hence, the same reference numerals will be assigned to components having the same functions as those described in the first embodiment, and the description thereof will not be repeated.

First, the conversion function 109c according to the second embodiment searches the first X-ray image generated by the image generation function 109b for a region to be colored in the same color when being displayed on the display 106. For example, the conversion function 109c extracts the color (level in the gradation of the image) of each of the pixels of the first X-ray image, and acquires the color after the conversion in the case where the color reduction LUT for display is applied. The conversion function 109c extracts the region to be the same color after the conversion. The region extracted here is a region in which pixels to be the same color after the conversion continue, and has a predetermined size. As an example, the conversion function 109c extracts a region in which a predetermined number of pixels to be the same color continue. Then, the conversion function 109c applies the pseudo gradation processing to the region to be the same color after being subjected to the color reduction. For example, the conversion function 109c converts the gradation of the pixels included in the extracted region into the display patterns based on the correspondence information.

Figure 10:
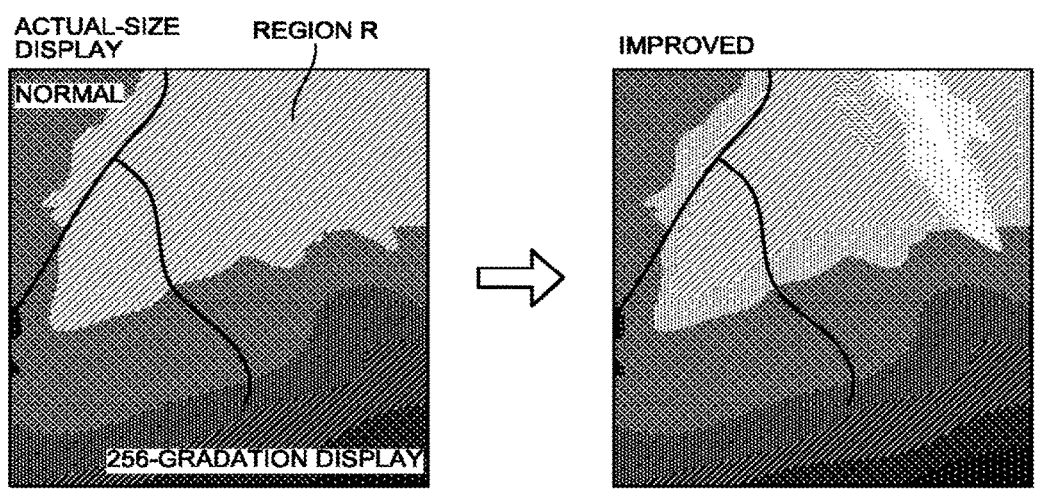
FIG. 10 is a diagram for explaining the gradation interpolation mode according to a second embodiment.

The following describes the gradation interpolation mode according to the second embodiment, using FIG. 10. FIG. 10 is a diagram for explaining the gradation interpolation mode according to the second embodiment. The left diagram of FIG. 10 illustrates an image before being processed, and the right diagram of FIG. 10 illustrates the image after being processed. For example, the conversion function 109c searches the X-ray image generated by the image generation function 109b for the region to be the same color in the case where the color reduction LUT for display is applied, and extracts a region R illustrated in FIG. 10. Then, the conversion function 109c performs the pseudo gradation processing on the pixels included in the extracted region R. The image generation function 109b generates the second X-ray image that expresses the region R as the display patterns converted by the pseudo gradation processing. As a result, the region R of an image displayed by the display control function 109d serves as an image containing the original gradation information, as illustrated in the right diagram of FIG. 10.

The region to be the same color refers to a region of pixels of the first X-ray image that correspond to pixels having gradation levels that are to be replaced with the same level in the gradation of the display 106 after being converted via the color reduction LUT for display included in the display 106. For example, in some cases where the X-ray image that has been "10-bits" original data is displayed on the "8-bits" display 106, the gradation levels of all pixels in the region that have been expressed at a plurality of levels at the stage of the original data are replaced with the same level in the gradation of the display 106, and all the pixels are displayed in the same color on the display 106, as illustrated as the region R in the left diagram of FIG. 10. Hereinafter, the region to be the same color (such as the region R illustrated in the left diagram of FIG. 10) will also be referred to as an identical replacement region.

Figure 11:
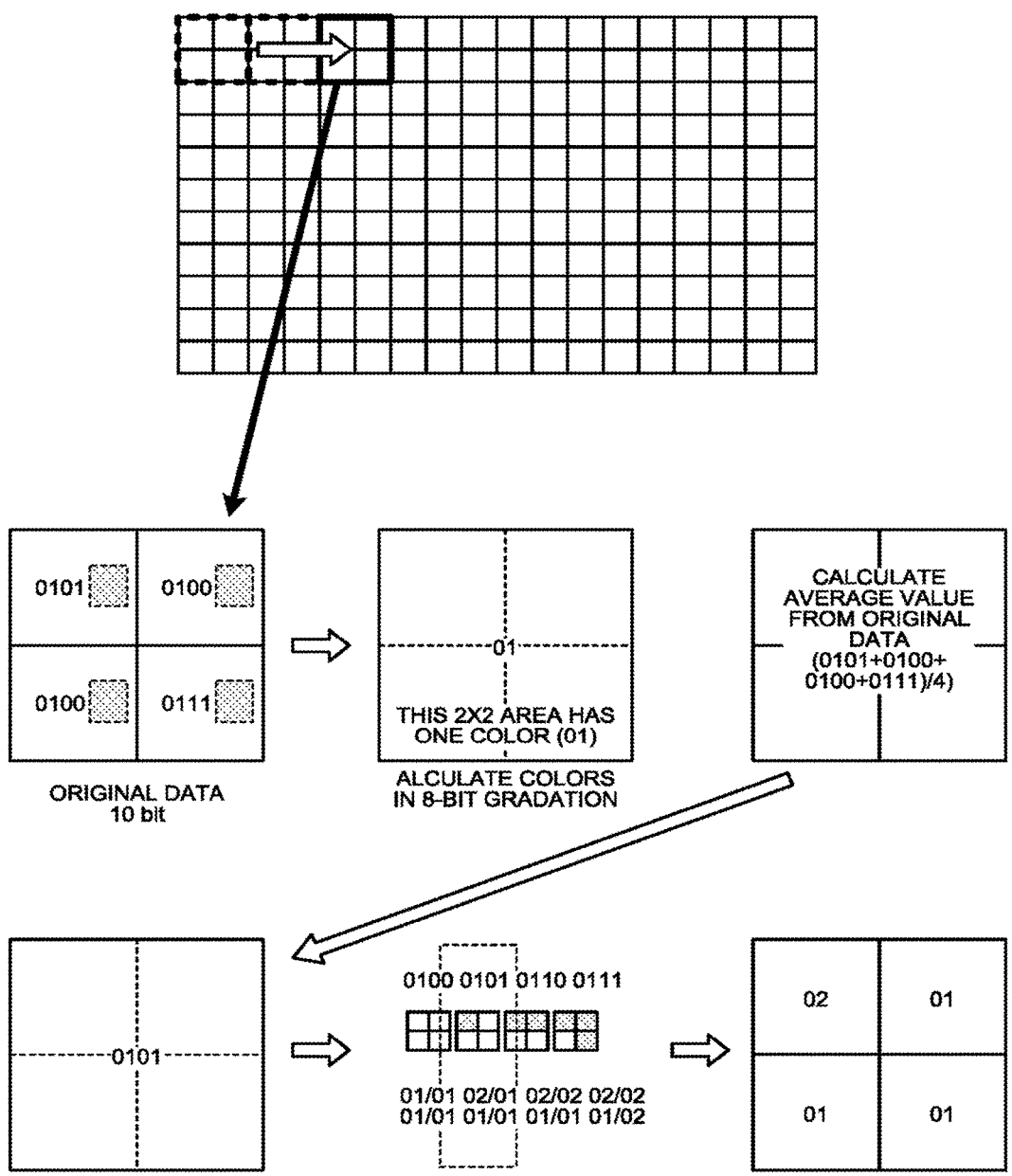
FIG. 11 is a diagram for explaining the gradation interpolation mode according to the second embodiment.

The following describes details of the processing performed by the conversion function 109c according to the second embodiment, using FIG. 11. FIG. 11 is a diagram for explaining the gradation interpolation mode according to the second embodiment. FIG. 11 illustrates the X-ray image generated by the image generation function 109b pixel by pixel. For example, as illustrated in the upper diagram of FIG. 11, the conversion function 109c extracts an area of "2×2" sequentially from a tip end on an edge of the X-ray image, and, if all pixels in the extracted area are to be the same color by being reduced in the number of colors to have the "8-bits" gradation that is the gradation of the display 106, identifies the pixels included in the extracted area as pixels to be the same color after being subjected to the color reduction. Hereinafter, the color of each pixel will be represented by a value expressed in a binary number.

For example, as illustrated in the lower diagram of FIG. 11, the colors of four pixels included in the area of "2×2" are assumed to be "0101", "0100", "0100", and "0111" at the stage of the "10-bits" original data. If the simple color reduction using the color reduction LUT for display is performed to output the "10-bits" original data to the "8-bits" display 106, the colors of all the pixels are to be replaced with the same color of "01", as illustrated in the lower diagram of FIG. 11. Hence, the conversion function 109c identifies the four pixels illustrated in the lower diagram of FIG. 11 as pixels to be the same color after being subjected to the color reduction.

Then, the conversion function 109c calculates the average value of the four pixel values identified at the stage of the "10-bits" original data in the "10-bits". For example, as illustrated in FIG. 11, the conversion function 109c calculates the average value of the four pixel values as "((0101+ 0100+0100+0111)/4)=0101". Then, the conversion function 109c replaces the calculated average value "0101" with a corresponding display pattern in the "8-bits" gradation. For example, as illustrated in the lower diagram of FIG. 11, the conversion function 109c replaces the average value "0101" with a display pattern in which the colors of the four pixels are "02", "01", 01", and "01". In other words, as illustrated in the lower diagram of FIG. 11, the conversion function 109c performs the pseudo gradation processing, for example, on each set of the four pixels included in the area of "2×2" in the first X-ray image. Consequently, the conversion function 109c can perform the pseudo gradation processing without changing the matrix (number of pixels) from that of the original image data.

In other words, based on the correspondence information, the conversion function 109c segments the pixels included in the identical replacement region into a plurality of pixel groups each including the number of pixels in the display pattern, and replaces the pixels included in each of the pixel groups with the display pattern corresponding to the level of gradation represented by the pixel group. For example, first, the conversion function 109c segments the pixels included in the region illustrated in the upper diagram of FIG. 11 into a plurality of pixel groups each including "four pixels" serving as the number of pixels in the display pattern. Then, the conversion function 109c replaces the segmented "four pixels" with the display pattern corresponding to the level of gradation represented by the "four pixels" (such as "0101" serving as the average value of colors of the "four pixels"). The image generation function 109b generates the second X-ray image that expresses the identical replacement region in the first X-ray image as the display patterns converted by the conversion function 109c.

Figure 12:
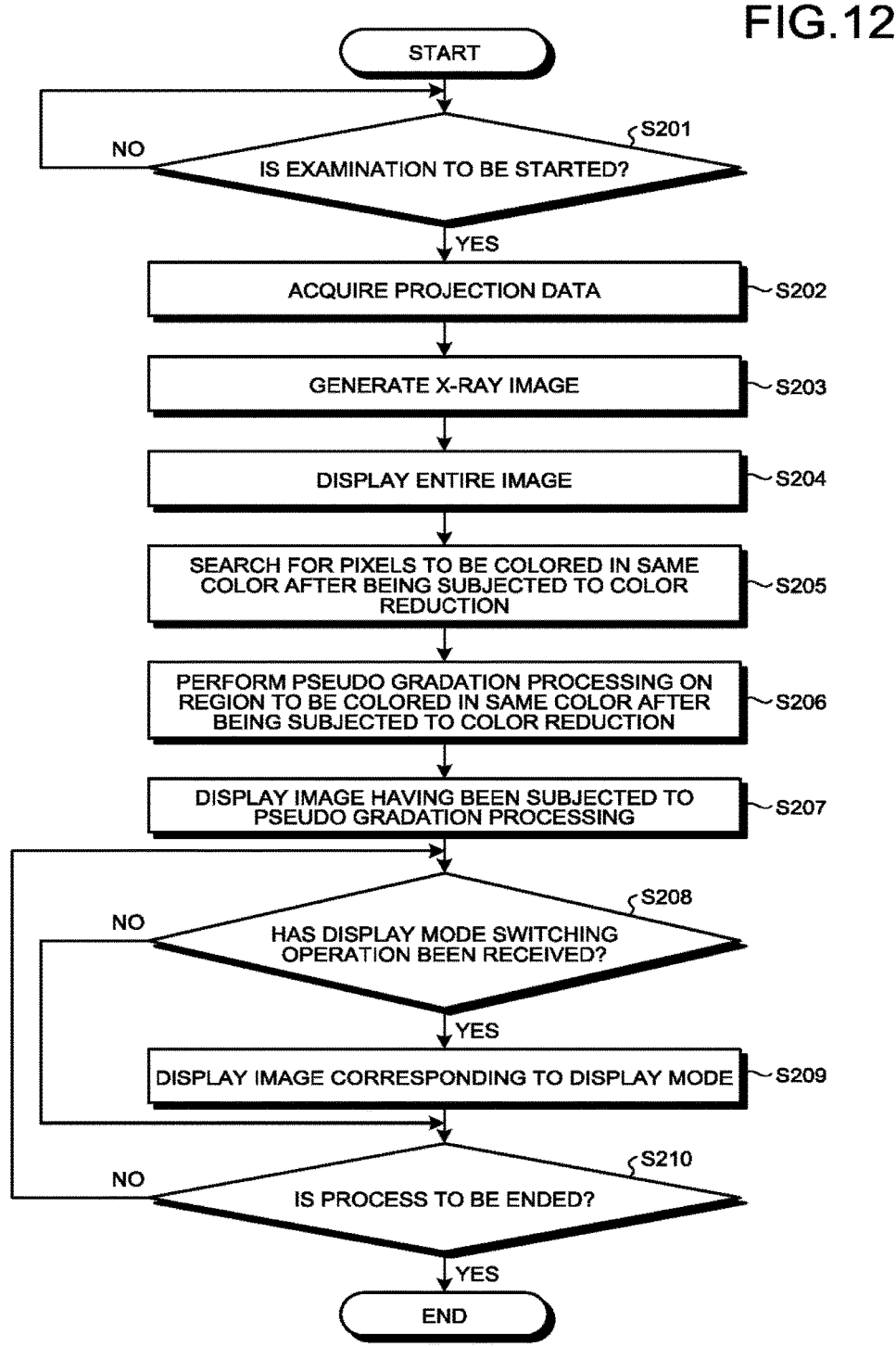
FIG. 12 is a flowchart for explaining a sequence of processing of the X-ray diagnostic apparatus according to the second embodiment.

The following describes an exemplary procedure of the processing performed by the X-ray diagnostic apparatus 1, using FIG. 12. FIG. 12 is a flowchart for explaining the sequence of the processing of the X-ray diagnostic apparatus 1 according to the second embodiment. Steps S201, S202, and S210 are steps corresponding to the control function 109a. Step S203 is a step corresponding to the image generation function 109b. Steps S205 and S206 are steps corresponding to the conversion function 109c and the image generation function 109b. Steps S204, S207, S208, and S209 are steps corresponding to the display control function 109d.

First, the processing circuitry 109 determines whether the examination start request has been received from the operator (Step S201). If not (No at Step S201), the processing circuitry 109 is placed in the waiting state. If so (Yes at Step S201), the processing circuitry 109 acquires projection data of the subject P (Step S202), and generates the X-ray image based on the signals acquired from the subject P (Step S203).

Then, the processing circuitry 109 displays the entire generated X-ray image on the display 106 (Step S204). The processing circuitry 109 searches the entire generated X-ray image for pixels to be the same color after being subjected to the color reduction (Step S205), and performs the pseudo gradation processing on the region in the X-ray image to be the same color after being subjected to the color reduction to generate the second X-ray image (Step S206). The processing circuitry 109 displays the second X-ray image having been subjected to the pseudo gradation processing on the display 106 (Step S207).

The processing circuitry 109 determines whether the switching operation of the display mode has been received (Step S208). If so (Yes at Step S208), the processing circuitry 109 displays the X-ray image having been subjected to the pseudo gradation processing or the X-ray image not having been subjected to the pseudo gradation processing, depending on the content of the operation, on the display 106 (Step S209). If not (No at Step S208), the processing circuitry 109 determines whether the end command has been received from the operator (Step S210). If not (No at Step S210), the processing circuitry 109 performs the processing of Step S208 again. If so (Yes at Step S210), the processing circuitry 109 ends the process.

As describe above, according to the second embodiment, the image generation function 109b generates the first X-ray image in which each of the pixels is expressed with the first gradation based on the X-rays transmitted through the subject P. Based on the correspondence information that associates each level of the first gradation with the display pattern of a plurality of pixels in the display 106 displayed with the second gradation having fewer levels than the first gradation, the conversion function 109c segments the pixels included in the identical replacement region in the first X-ray image having gradation levels that are to be replaced with the same level in the second gradation into a plurality of pixel groups each including the number of pixels in the display pattern, and converts the pixels included in each of the pixel groups into the display pattern corresponding to the level in the first gradation represented by the pixel group. The image generation function 109b generates the second X-ray image that expresses the identical replacement region in the first X-ray image as the display patterns converted by the conversion function 109c. The display control function 109d displays the second X-ray image on the display 106. Consequently, the X-ray diagnostic apparatus 1 according to the second embodiment presents, to the operator, the information that will be lost if the simple color reduction is performed in the display 106, and thus can improve the accuracy of the examinations using the X-ray image.

As described above, the conversion function 109c according to the second embodiment searches for the pixels to be the same color by the color reduction in the display 106, and performs the pseudo gradation processing on the region to be the same color in the first X-ray image. Consequently, the X-ray diagnostic apparatus 1 according to the second embodiment can allow regions (such as the regions other than the region R in the left diagram of FIG. 10) that are not colored in the same color via the LUT in the display 106 to be displayed and compared in a conventional way using the original image data without performing the pseudo gradation processing.

The conversion function 109c according to the second embodiment performs the pseudo gradation processing while maintaining the number of pixels (matrix size) of the X-ray image. Consequently, even in the case where increasing the number of pixels of the X-ray image makes the display on the display 106 difficult due to the relation between the number of pixels of the display 106 and the number of pixels of the X-ray image, the X-ray diagnostic apparatus 1 according to the second embodiment presents the X-ray image having been subjected to the pseudo gradation processing to the operator, and thus can improve the examination accuracy.

In the first and second embodiments described above, the case has been described where the pseudo gradation processing is applied to the first X-ray image. Instead, in a third embodiment, a case will be described where a plurality of corrected images are generated based on a plurality of such first X-ray images generated along time, and the pseudo gradation processing is applied to the generated corrected images. The X-ray diagnostic apparatus 1 according to the third embodiment differs from the X-ray diagnostic apparatus 1 according to the first embodiment illustrated in FIG. 1 in that the processing circuitry 109 further includes a feature point position detection function and a corrected image generation function, which are to be described later. The X-ray diagnostic apparatus 1 according to the third embodiment partially also differs from the X-ray diagnostic apparatus 1 according to the first embodiment illustrated in FIG. 1 in the processing performed in the image generation function 109b, the conversion function 109c, and the region specification function 109e. The same reference numerals in FIG. 1 will be assigned to components having the same functions as those described in the first embodiment, and the description thereof will not be repeated.

The feature point position detection function in the third embodiment is an example of feature point position detection processing performed by the processing circuitry described in the claims. The corrected image generation function in the third embodiment is an example of corrected image generation processing performed by the processing circuitry described in the claims.

First, the feature point position detection function in the processing circuitry 109 detects positions of the feature points in each of the first X-ray images generated along time by the image generation function 109b. The feature points are, for example, the stent markers included in the first X-ray image. For example, the feature point position detection function calculates coordinates of the stent markers in images in which the stent markers are located, for each plurality of such first X-ray images. Then, based on the first X-ray images, the corrected image generation function generates the corrected images in which the positions of the feature points are substantially the same among the first X-ray images.

For example, the corrected image generation function corrects the first X-ray images so as to match the coordinates of the stent markers among the first X-ray images, and thus generates the corrected images. As an example, assuming the coordinates of a stent marker in any X-ray image of the first X-ray images (such as a temporally first one of the X-ray images) as reference coordinates, the corrected image generation function applies image deformation processing, such as image movement processing including translation and rotation, and an affine transformation, to each of the first X-ray images so as to match the coordinates of the stent markers in the first X-ray image with the reference coordinates, and thus generates the corrected images.

Alternatively, the corrected image generation function aligns the positions of a plurality of X-ray images included in the first X-ray images with one another based on the positions of the feature points in the images, and adds the X-ray images together to generate the corrected images. In other words, the corrected image generation function applies a recursive filter to the first X-ray images to generate the corrected images. The recursive filter is an example of a high-frequency noise reduction filter.

As an example, the corrected image generation function first corrects the first X-ray images so as to match the coordinates of the stent markers in the images among the first X-ray images. Then, the corrected image generation function performs processing, such as arithmetic averaging, on the X-ray images in the first X-ray images after being corrected to generate the corrected images. For example, if the first X-ray images are three X-ray images of the "X-ray image at time T1", the "X-ray image at time T2", and the "X-ray image at time T3", the corrected image generation function generates a corrected image acquired by adding together the "X-ray image at time T1" to the "X-ray image at time T2" and a corrected image acquired by adding together the "X-ray image at time T2" to the "X-ray image at time T3".

Any number of X-ray images of the first X-ray images may be used to generate one corrected image. The number of the X-ray images may be set by the operator, or set to a preset value, or set by the corrected image generation function based on, for example, levels of variations in the coordinates of the stent markers between the first X-ray images before being corrected. When the first X-ray images are added together to generate the corrected images, the pixel values of the pixels constituting the first X-ray images may be weighted. For example, the corrected image generation function adds the first X-ray images acquired along time together so that the pixel values of temporally closer first X-ray images have larger weights.

Then, the region specification function 109e specifies partial regions in the corrected images. The region specification function 109e may specify a partial region for each of the corrected images, or may specify one partial region for the corrected images. For example, since the coordinates of the stent markers in the corrected images match among the corrected images, the region specification function 109e can specify the partial regions in the corrected images by specifying regions with respect to the coordinates of the stent markers serving as the references (such as regions having predetermined sizes and shapes centered around the coordinates of the stent markers).

Then, the conversion function 109c converts the level in the first gradation of each of the pixels included in the partial region in each of the corrected images into the corresponding display pattern based on the correspondence information that associates each level of the first gradation with the display pattern of a plurality of pixels in the display 106 displayed with the second gradation having fewer levels than the first gradation. In the third embodiment, the gradation represented by each of the pixels in the corrected images generated by the corrected image generation function is referred to as the first gradation. The gradation represented by each of the pixels of the first X-ray images may be the same as the first gradation represented by each of the pixels in the corrected images.

The image generation function 109b generates the second X-ray image that expresses the pixels included in the partial regions of the corrected images as the display patterns converted by the conversion function 109c. In other words, the image generation function 109b generates the second X-ray image that expresses, as the display patterns, the pixels in the partial regions of the corrected images generated by correcting the first X-ray images so as to match the coordinates of the stent markers among the first X-ray images, or generates the second X-ray image that expresses, as the display patterns, the pixels in the partial regions of the corrected images generated by aligning the positions of the X-ray images included in the first X-ray images with one another based on the positions of the feature points in the images, and adding the X-ray images together. The display control function 109d displays the second X-ray image on the display 106.

As an example of generating the second X-ray image by applying the recursive filter and the dithering to the first X-ray images, the case has been described heretofore where the images aligned in position based on the positions of the stent markers are added together to generate the corrected images, and the dithering is applied to the partial regions of the generated corrected images. The embodiments are, however, not limited to this example. For example, a case may exist where the first X-ray images are aligned in position based on the positions of the stent markers to generate the corrected images, and, after the dithering is applied to the partial regions of the generated corrected images, the corrected images after being dithered are added together.

In some cases where the recursive filter is applied, the addition processing may be applied while background portions other than the stent markers in the images is misaligned in position, and consequently, visibility of the background portions may be reduced. In particular, the visibility of the background portions is reduced with increase in the number of added images. The number of added images in the recursive filter can be reduced by applying the recursive filter and then applying the dithering to the first X-ray image, or by applying the dithering and then applying the recursive filter to the first X-ray image. For example, in some cases, such as a case where the stepwise noise illustrated in FIG. 6B is generated, high-frequency noise may significantly increase due to the color reduction at the stage of display. The high-frequency noise can, however, be reduced by the dithering to express the information on the gradation lost by the color reduction on the display 106. Consequently, the high-frequency noise can be sufficiently reduced even if the number of added images is reduced. As a result, the number of images added together by the recursive filter can be reduced, and thus, the visibility of the background portions can be improved.

In the first to third embodiments described above, the case has been described where the display 106 is a color monitor that displays the image with the gradation of 8-bits (256 gradation levels) for each of the RGB colors. The embodiments are, however, not limited to this case. For example, the display 106 may be a black-and-white monitor, and the number of gradation levels is not limited to the 8-bits levels.

In the first to third embodiments described above, the case has been described where the image generation function 109b generates the second X-ray image, and then the display control function 109d displays the second X-ray image on the display 106. The embodiments are, however, not limited to this case. For example, a case may exist where the image generation function 109b generates the second X-ray image, and then the second X-ray image is stored in the memory circuitry 108 without being displayed. The second X-ray image stored in the memory circuitry 108 is, for example, read out by the X-ray diagnostic apparatus 1 or another device, and is displayed on the display 106 or another display.

In the first to third embodiments described above, the case has been described where the processing circuitry 109 performs the image processing on the first X-ray image generated by the image generation function 109b. The embodiments are, however, not limited to this case. For example, a case may exist where the processing circuitry 109 acquires the first X-ray image from, for example, a database of another X-ray diagnostic apparatus or a picture archiving and communication system (PACS), or the database of an electronic medical chart system, and performs the image processing on the acquired first X-ray image.

In other words, the processing circuitry 109 is provided with an acquisition function to acquire the first X-ray image. The image generation function 109b generating the first X-ray image is an example of the acquisition function in the processing circuitry 109. The acquisition function is an example of acquisition processing performed by the processing circuitry described in the claims. The processing circuitry 109 can perform the image processing on the first X-ray image generated based on the X-rays transmitted through the subject and the first X-ray image acquired from, for example, the other X-ray diagnostic apparatus, any of various databases, and the like.

A case may exist where the image processing method described above is performed by an image processing apparatus installed independently of the X-ray diagnostic apparatus. For example, a case may exist where an image processing apparatus having the same functions as those of the processing circuitry 109 illustrated in FIG. 1 performs the image processing method described above using the image data acquired from the X-ray diagnostic apparatus, the database of the PACS, the database of the electronic medical chart system, and the like.

For example, the image processing apparatus independent of the X-ray diagnostic apparatus acquires the first X-ray image from the other X-ray diagnostic apparatus or the database of the PACS and the like, and applies the dithering to the acquired first X-ray image so as to generate the second X-ray image and display the generated the second X-ray image on any display. For example, the image processing apparatus independent of the X-ray diagnostic apparatus is installed in or brought into a room where a conference is to be held, and is connected to a display used for image display in the conference. The image processing apparatus determines, according to the gradation displayable by the connected display, whether to perform the dither processing. For example, if the acquired first X-ray image is a "10-bits" image and the connected display is an "8-bits" color monitor, the image processing apparatus determines to perform the dither processing, and generates and displays the dithered second X-ray image on the display.

The image processing apparatus described above may be what is called a video card (also called a graphics board). For example, the video card is added to a PC provided with a display. In such a case, the video card applies the dithering to the first X-ray image acquired from the PC, and generates and displays the second X-ray image on the display.

If the display 106 is a display screen of a portable terminal, such as a tablet computer, a device separate from the portable terminal may perform the image processing method described above, or the portable terminal may perform the image processing method described above.

The components of the devices according to the first to third embodiments are functionally conceptual, and need not be physically configured as illustrated in the drawings. In other words, the specific mode of dispersion and integration of the devices is not limited to those illustrated in the drawings, and all or some of the devices can be configured in a functionally or physically dispersed or integrated manner in any units according to various types of loads or use conditions. Furthermore, all or any part of the processing functions performed in the devices can be implemented by a CPU and a program to be analyzed and executed by the CPU, or can be implemented as hardware with a wired logic.

The image processing method described in the first to third embodiments can be performed by executing an image processing program provided in advance on a computer, such as a personal computer or a workstation. This image processing program can be distributed through a network, such as the Internet. This image processing program can also be executed by recorded on a computer-readable recording medium, such as a hard disk, a flexible disk (FD), a compact disc read-only memory (CD-ROM), a magneto-optical (MO) disk, or a digital versatile disc (DVD), and by being read by a computer from the recording medium.

According to at least one of the embodiments described above, the accuracy of the examinations using the image can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
processing circuitry configured to
acquire a first image in which each pixel is expressed with a first gradation;
specify a partial region in the first image;
convert, based on correspondence information that associates each level of the first gradation with a display pattern of a plurality of pixels on a display, the level of the first gradation of each pixel included in the partial region in the first image into the corresponding display pattern, the display displaying the display pattern with a second gradation having fewer levels than the first gradation; and
generate a second image that expresses a plurality of first pixels included in the partial region of the first image as the converted display patterns.

2. The image processing apparatus according to claim 1, wherein the processing circuitry is further configured to:
receive an operation to an image that has been acquired by replacing each level of the first gradation of each pixel in the first image with a corresponding level in the second gradation, and displayed on the display; and
specify the partial region based on the received operation.

3. The image processing apparatus according to claim 1, wherein the processing circuitry is further configured to:
set a region of interest in the first image; and
determine, according to information on a device included in the region of interest, whether to specify the region of interest as the partial region.

4. The image processing apparatus according to claim 3, wherein
the device is a stent, and
the processing circuitry is further configured to determine, based on an image of the stent in the region of interest, whether to specify the region of interest as the partial region.

5. The image processing apparatus according to claim 4, wherein the processing circuitry is further configured to acquire a mesh density of the stent based on the image of the stent in the region of interest, and determine, based on the acquired mesh density, whether to specify the region of interest as the partial region.

6. The image processing apparatus according to claim 3, further comprising input circuitry configured to receive an input operation from an operator, wherein
the device is a stent,
the input circuitry is configured to receive the input operation of information on the stent, and
the processing circuitry is configured to determine, based on the received information on the stent, whether to specify the region of interest as the partial region.

7. The image processing apparatus according to claim 3, wherein the processing circuitry is further configured to set the region of interest based on a feature point included in the first image.

8. The image processing apparatus according to claim 1, wherein the processing circuitry is further configured to:
set a region of interest in the first image; and
determine, according to whether the region of interest includes a device, whether to specify the region of interest as the partial region.

9. The image processing apparatus according to claim 8, wherein
the device is a line-shaped device, and
the processing circuitry is further configured to specify the region of interest as the partial region when the region of interest does not include the line-shaped device.

10. The image processing apparatus according to claim 1, wherein the processing circuitry is further configured to specify the partial region based on annotation information attached to the first image.

11. The image processing apparatus according to claim 10, wherein the annotation information is information indicating a tumor or information detected by a computer aided diagnosis.

12. An image processing apparatus, comprising:
processing circuitry configured to
acquire a first image in which each pixel is expressed with a first gradation;
segment, based on correspondence information that associates each level of the first gradation with a display pattern of a plurality of pixels on a display, pixels included in an identical replacement region in the first image having gradation levels that are to be replaced with a same level in a second gradation into a plurality of pixel groups each including a number of pixels in the display pattern, and convert a plurality of pixels included in each of the pixel groups into the display pattern corresponding to the level in the first gradation represented by the pixel group, the display displaying the display pattern with the second gradation having fewer levels than the first gradation; and
generate a second image that expresses an identical replacement region in the first image as the converted display patterns.

13. The image processing apparatus according to claim 12, wherein the processing circuitry is further configured to set an average value of levels in the first gradation of the pixels included in the pixel group as the level in the first gradation represented by the pixel group.

14. The image processing apparatus according to claim 1, wherein the processing circuitry is further configured to switch, according to a switching operation of a display mode of an image, between a third image acquired by replacing each level of the first gradation of each pixel in the first image with a corresponding level in the second gradation and the second image, and display an image selected by the switching on the display.

15. An image processing apparatus, comprising:
processing circuitry configured to
acquire a plurality of first images generated in a time series;
detect a position of a feature point in each of the first images;
generate, based on the first images, a plurality of corrected images in which the positions of the feature points are substantially a same among the first images and each pixel is expressed with a first gradation;
specify partial regions in the corrected images;
convert, based on correspondence information that associates each level of the first gradation with a display pattern of a plurality of pixels on a display, the level of the first gradation of each pixel included in the partial regions in the corrected images into the corresponding display pattern, the display displaying the display pattern with a second gradation having fewer levels than the first gradation; and
generate a second image that expresses a plurality of first pixels included in the partial regions of the corrected images as the converted display patterns.

16. The image processing apparatus according to claim 15, wherein the processing circuitry is further configured to align positions of a plurality of images included in the first images with one another based on the positions of the feature points in the images, and add the plurality of images together to generate the corrected images.

17. The image processing apparatus according to claim 1, wherein each of the first gradation and the second gradation is a gradation in brightness of hues expressed in an image.

18. The image processing apparatus according to claim 1, wherein the display is a display screen of a portable terminal.

* * * * *